United States Patent
Tobe et al.

(10) Patent No.: US 7,781,223 B2
(45) Date of Patent: Aug. 24, 2010

(54) MOLECULAR-WIRE TYPE FLUORESCENT CHIRAL SENSOR

(75) Inventors: Yoshito Tobe, Ashiya (JP); Keiji Hirose, Toyono-gun (JP)

(73) Assignee: Japan Science and Technology Agency (JP)

( * ) Notice: Subject to any disclaimer, the term of this patent is extended or adjusted under 35 U.S.C. 154(b) by 368 days.

(21) Appl. No.: 10/591,920

(22) PCT Filed: Nov. 22, 2004

(86) PCT No.: PCT/JP2004/017675

§ 371 (c)(1),
(2), (4) Date: Sep. 7, 2006

(87) PCT Pub. No.: WO2005/087835

PCT Pub. Date: Sep. 22, 2005

(65) Prior Publication Data

US 2007/0179272 A1 Aug. 2, 2007

(30) Foreign Application Priority Data

Mar. 10, 2004 (JP) ............................. 2004-067226

(51) Int. Cl.
*G01N 21/76* (2006.01)
(52) U.S. Cl. ...................... 436/172; 436/106; 436/107; 436/164; 549/347
(58) Field of Classification Search ................. 436/172
See application file for complete search history.

(56) References Cited

U.S. PATENT DOCUMENTS

| 5,405,975 | A | 4/1995 | Kuhn et al. |
| 7,358,403 | B2 | 4/2008 | Tobe et al. |
| 2005/0227366 | A1 | 10/2005 | Tobe et al. |

FOREIGN PATENT DOCUMENTS

| JP | 61-207414 A | 9/1986 |
| JP | 7-097450 A | 4/1995 |
| JP | 10-120914 A | 5/1998 |
| JP | 2003-292538 A | 10/2003 |
| JP | 2004-75624 A | 3/2004 |

OTHER PUBLICATIONS

Kim, et al. "Ion-Specific Aggregation in Conjugated Polymers: Highly Sensitive and Selective Fluorescent Ion Chemosensors", Angew. Chem Int Ed, 2000, vol. 39, No. 21, pp. 3868-3872.*

Naemura, et al. "Temperature dependent reversal of enantiomer selectivity in the complexation of optically active phenolic crown ethers with chiral amines", Chem. Commun. 1996, pp. 2749-2750.*

Swager, Timothy M., "The Molecular Wire Approach to Sensory Signal Amplification", *Accounts of Chemical Research*, 1998, pp. 201-207, vol. 31, No. 5, American Chemical Society.

Ohki, Ichiro and Tobe, Yoshito, "High Sensitive Sensors Using Molecular Wires", *Chemistry*, 2001, pp. 62-63, vol. 56, with partial English translation.

Zhou, Qin and Swager, Timothy M., "Methodology for Enhancing the Sensitivity of Fluorescent Chemosensors: Energy Migration in Conjugated Polymers", *Journal American Chemical Society*, 1995, pp. 7017-7018, vol. 117, American Chemical Society.

Zhou, Qin and Swager, Timothy M., "Fluorescent Chemosensors Based on Energy Migration I Conjugated Polymers: The Molecular Wire Approach to Increased Sensitivity", *Journal American Chemical Society*, 1995, pp. 12593-12602, vol. 117, American Chemical Society.

Crawford, Khushrav B.; Goldfinger, Marc B.; and Swager, Timothy M., "$Na^+$ Specific Emission Changes in an Ionophoric Conjugated Polymer", *Journal American Chemical Society*, 1998, pp. 5187-5192, vol. 120, American Chemical Society.

Yang, Jye-Shane and Swager, Timothy M., "Porous Shape Persistent Fluorescent Polymer Films: An Approach to TNT Sensory Materials", *Journal American Chemical Society*, 1998, pp. 5321-5322, vol. 120, American Chemical Society.

Yang, Jye-Shane and Swager, Timothy M., "Fluorescent Porous Polymer Films as TNT Chemosensors: Electronic and Structural Effects", *Journal American Chemical Society*, 1998, pp. 11864-11873, vol. 120, American Chemical Society.

Kim, Jinsang; McQuade, Tyler; McHugh, Sean K; and Swager, Timothy M, "Ion-Specific Aggregation in Conjugated Polymers: Highly Sensitive and Selective Fluorescent Ion Chemosensors", *Angew. Chem. Int. Ed.*, 2000, pp. 3868-3872, vol. 39, No. 21, Wiley-VCH Verlag GmbH, Germany.

Hirose, Keiji et al., "Preparation of Phenolic Chiral Crown Ethers and Podands and Their Enantiomer Recognition Ability Toward Secondary Amines", Tetrahedron: Assymmetry, (2003), pp. 555-566, vol. 14, Elsevier Science Ltd.
Kaneda, T., et al., J. Am. Chem. Soc. 1989, 111, 742-743.
Sawada, M., et al., J. Am. Chem. Soc. 1993, 115, 7381-7388.
Naemura, K., et al., Tetrahedron:Asymmetry 1994, 5, 1549-1558.
Sawada, M., et al., J. Chem. Soc., Chem. Commun. 1994, 2497-2498.
Naemura, K., et al., Tetrahedron:Asymmetry 1997, 8, 19-22.
Hirose, K., et al., J. Chem. Soc., Perkin Trans. 2 1997, 1649-1657.
Naemura, K., et al., Tetrahedron:Asymmetry 1998, 9, 563-574.
Hirose, K., et al., Tetrahedron:Asymmetry 2003, 14, 555-566.
Naemura, K., et al., J. Chem. Soc., Perkin Trans. 1 1996, 383-388.
Shorygin, P. P., et al., Russ. Chem. Bull. 1998, 47, 297-302.
Koch, R., et al., J. Phys. Org. Chem. 2008, 21, 954-962.
Sitha, S., et al., J Mol Struc-Theochem 2006, 761, 31-38.
Nakashima, K., et al., Bull. Chem. Soc. Jpn. 1987, 60, 3219-3223.
Tanigawa, I., et al., Tetrahedron Lett. 1984, 25, 5327-5330.
Forrest, H., et al., Talanta 1989, 36, 335-340.
Desilva, A. P., et al., J. Chem. Soc., Chem. Commun. 1989, 1183-1185.
Crossley, R., et al., J. Chem. Soc., Perkin Trans. 1994, 2, 513-520.

\* cited by examiner

*Primary Examiner*—Yelena G Gakh
*Assistant Examiner*—David Weisz
(74) *Attorney, Agent, or Firm*—The Webb Law Firm

(57) ABSTRACT

A fluorescent molecular wire is provided, having a fluorescent polymer main chain to which an optically active substituent is linked so as to be conjugatable form, the optically active substituent being represented by formula (I) below:

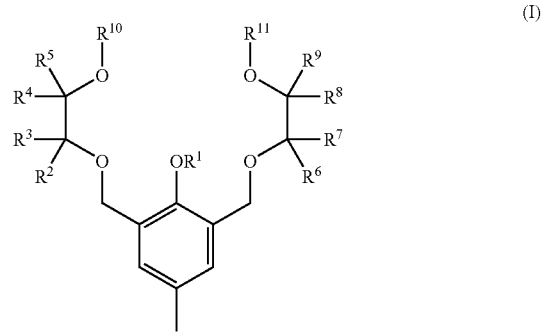

where $R^1$ represents a hydrogen atom or an alkyl group having 1 to 10 carbon atoms; $R^2$, $R^3$, $R^4$, $R^5$, $R^6$, $R^7$, $R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent; and $R^{10}$ and $R^{11}$ represent independently a hydrogen atom or an alkyl group having 1 to 15 carbon atoms that may have a heteroatom, and $R^{10}$ and $R^{11}$ may be bonded to form an alkylene group having 2 to 30 carbon atoms that may have a heteroatom.

13 Claims, 2 Drawing Sheets

MOLECULAR-WIRE TYPE FLUORESCENT CHIRAL SENSOR

TECHNICAL FIELD

The present invention relates to a chiral sensor constituted by an optically active compound. More specifically, the present invention relates to a molecular-wire type fluorescent chiral sensor into which an optically active portion that is capable of recognizing a chiral compound is introduced.

BACKGROUND ART

Pharmaceuticals having an optical isomer are required to be produced as optically pure compounds in view of side effects, for example. Therefore, optical resolution and optical purity test have become increasingly important. In particular, since optically active amines such as ethanolamine derivatives and catecholamine derivatives have physiological activities on the central nervous system, they are important compounds as intermediates for various pharmaceuticals. Moreover, natural amino acids and physiologically active substances are all chiral compounds. Thus, research on a variety of chiral sensors has been conducted for optical resolution and analytical purposes of the optically active amines.

The inventors previously have found out that optically active pseudo-18-crown-6 having a variety of metacyclophane structures, for example, have high asymmetry recognition ability toward primary amines (see Japanese Laid-Open Patent Publication No. 2004-75624).

For example, a selector that is represented by the following formula and in which pseudo-18-crown-6 is bound to a silica gel is applied to column chromatography and shows excellent separation ability toward a variety of primary amines.

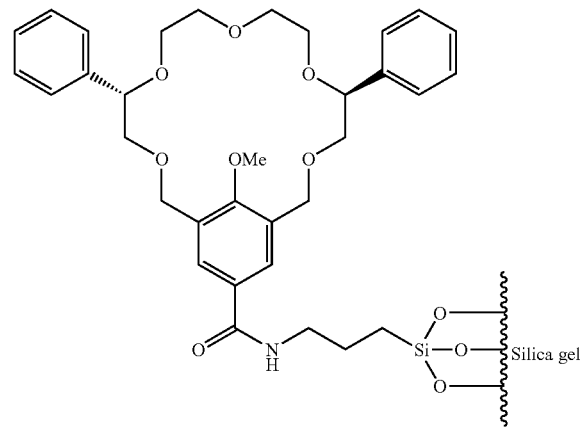

Moreover, the pseudo-18-crown-6 that is represented by the following formula and into which a 2,4-dinitrophenylazo group, which is a chromophore, is introduced changes its absorption spectrum significantly by forming a complex with an amine. As a result, the color is changed to such an extent that the change can be observed visually, so that this pseudo-18-crown-6 can be used as a chiral indicator. However, this pseudo-18-crown-6 is still not sufficient as a chiral sensor in view of the detection sensitivity.

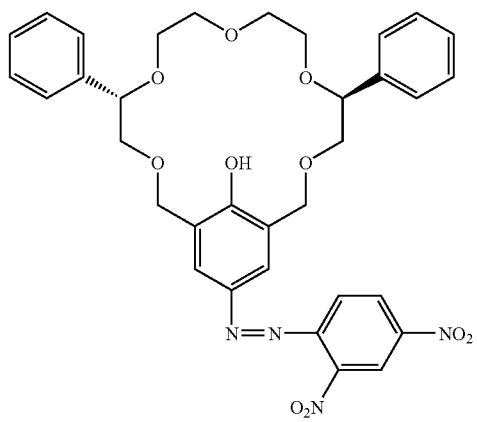

Chemical sensors such as chiral sensors are devices having a receptor site that recognizes a specific ion or molecule as a target and is bound thereto, and these devices read a change in the electronic state resulting from the binding to the target as an optical response (e.g., a change in absorption or fluorescence spectrum) or an electrical response (e.g., a change in electrical conductivity or oxidation-reduction potential). The sensitivity of the chemical sensors depends on the degree of binding ability between the target and the receptor site (complex stability constant) and the efficiency of converting the changes in the electronic state of a sensor molecule into signals. This will be described on the basis of the following scheme:

(A)

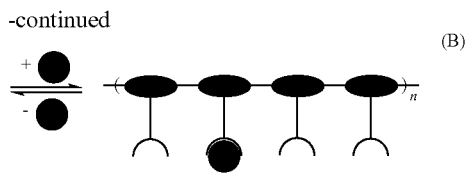

(B)

As shown in (A) of the scheme, usually, a signal is generated in one-to-one correspondence with a binding between the target and the receptor site. In order to increase the detection sensitivity, it is necessary to increase the complex stability constant so as to increase the number of targets to be bound, but the selectivity decreases. On the other hand, if a highly configured receptor site is used in order to improve the selectivity, then the complex forming rate is reduced, and thus a response cannot be provided quickly. To address this problem, a molecular wire method, which is a method for achieving a high sensitivity by increasing the signal conversion efficiency using a conjugated polymer, has been proposed ((B) of the scheme; see T. M. Swager, Acc. Chem. Res., vol. 31, p. 201, 1998; and Ichiro Ohki and Yoshito Tobe, Chemistry, vol. 56, p. 62, 2001).

When a conjugated polymer is used as in (B) of the scheme, receptor sites can be immobilized to a carrier, and furthermore electrons and holes or the excitation energy can move freely within an effective conjugated chain. For example, when the target is bound to any given portion of the receptor sites of a conductive polymer, the electronic state of the effective conjugated chain is changed, which results in a change in the electrical conductivity or the oxidation-reduction potential of the polymer (see (B) of the scheme). In the case of a fluorescent polymer, the excitation energy that moves in the conjugated chain is deactivated by the target bound to one receptor site, which results in a quenching of the fluorescence due to the polymer. In other words, whichever receptor site within the effective conjugated chain the target is bound to, an electrical or optical response can be obtained, so that a high sensitivity that conventional low molecular weight sensors have not provided can be achieved. Specifically, poly (p-phenylene ethynylene) or polythiophene having conductivity and strong fluorescence emission properties is used for the polymer main chain, and a host molecular framework such as electron-donative cyclophane or calixarene is used for the receptor site (see Q. Zhou and T. M. Swager, J. Am. Chem. Soc., vol. 117, p. 7017, 1995; Q. Zhou and T. M. Swager, J. Am. Chem. Soc., vol. 117, p. 12593, 1995; K. B. Crawford et al., J. Am. Chem. Soc., vol. 120, p. 5187, 1998; J.-S. Yang and T. M. Swager, J. Am. Chem. Soc., vol. 120, p. 5321, 1998; J.-S. Yang and T. M. Swager, J. Am. Chem. Soc., vol. 120, p. 11864, 1998; and J. Kim et al., Angew. Chem. Int. Ed., vol. 39, p. 3868, 2000).

SUMMARY OF INVENTION

It is an object of the present invention to provide a chiral amine sensor having high sensitivity and high asymmetry recognition ability.

The inventors of the present invention found that when a compound having high asymmetry recognition ability toward the above-mentioned primary amines was incorporated into a molecular wire as the receptor site, the obtained compound could actually function as a chiral amine sensor having high sensitivity, and thus achieved the present invention.

The present invention provides a fluorescent molecular wire including a fluorescent polymer main chain to which an optically active substituent is linked so as to be a conjugatable form, the optically active substituent being represented by the following formula (I):

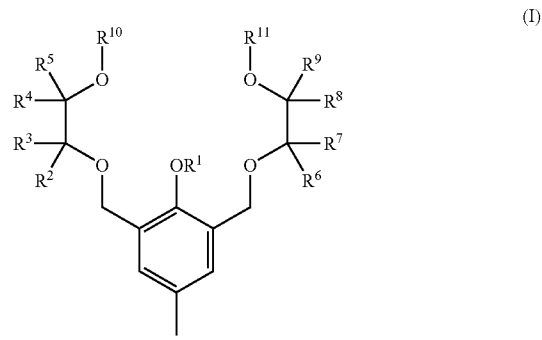

where $R^1$ represents a hydrogen atom or an alkyl group having 1 to 10 carbon atoms; $R^2$, $R^3$, $R^4$, $R^5$, $R^6$, $R^7$, $R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent; and $R^{10}$ and $R^{11}$ represent independently a hydrogen atom or an alkyl group having 1 to 15 carbon atoms that may have a heteroatom, and $R^{10}$ and $R^{11}$ may be bonded to form an alkylene group having 2 to 30 carbon atoms that may have a heteroatom.

In a preferred embodiment, the polymer main chain is a polyarylene structure, a poly(arylene ethynylene) structure, or a poly(arylene vinylene) structure, preferably, a polyphenylene structure, a polythiophene structure, a poly(phenylene thiophenylene) structure, a poly(phenylene ethynylene) structure, a poly(thiophenylene ethynylene) structure, or a poly(phenylene vinylene) structure.

In a more preferred embodiment, the optically active substituent is coupled to the polymer main chain via mono- or poly-arylene, mono- or poly-alkylene, mono- or poly-vinylene, or a combination thereof.

In a preferred embodiment, the optically active substituent is represented by the following formula (II):

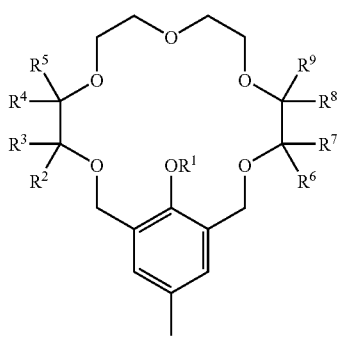

(II)

where $R^1$ represents a hydrogen atom or an alkyl group having 1 to 10 carbon atoms; and $R^2, R^3, R^4, R^5, R^6, R^7, R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent.

In a further preferred embodiment, the fluorescent molecular wire is represented by the following formula (III):

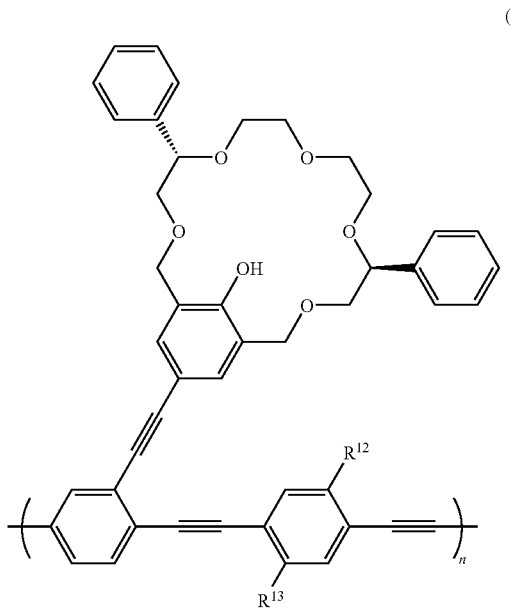

(III)

where $R^{12}$ and $R^{13}$ represent independently a hydrogen atom, an alkyl group having 1 to 20 carbon atoms, an alkoxy group having 1 to 20 carbon atoms, a di- or mono-alkylamide group having 1 to 20 carbon atoms, or an alkyl ester group having 1 to 20 carbon atoms; and n is an integer of 5 or more.

The present invention also provides a chiral sensor including any one of the fluorescent molecular wires described above.

The fluorescent molecular wire of the present invention has not only a higher detection sensitivity but also an improved asymmetry recognition ability when compared to monomeric compounds having the same structure as a substituent having high asymmetry recognition ability. Therefore, it can function as a primary amine chiral sensor having an even higher sensitivity and selectivity.

BEST MODE FOR CARRYING OUT THE INVENTION

Figure 1:
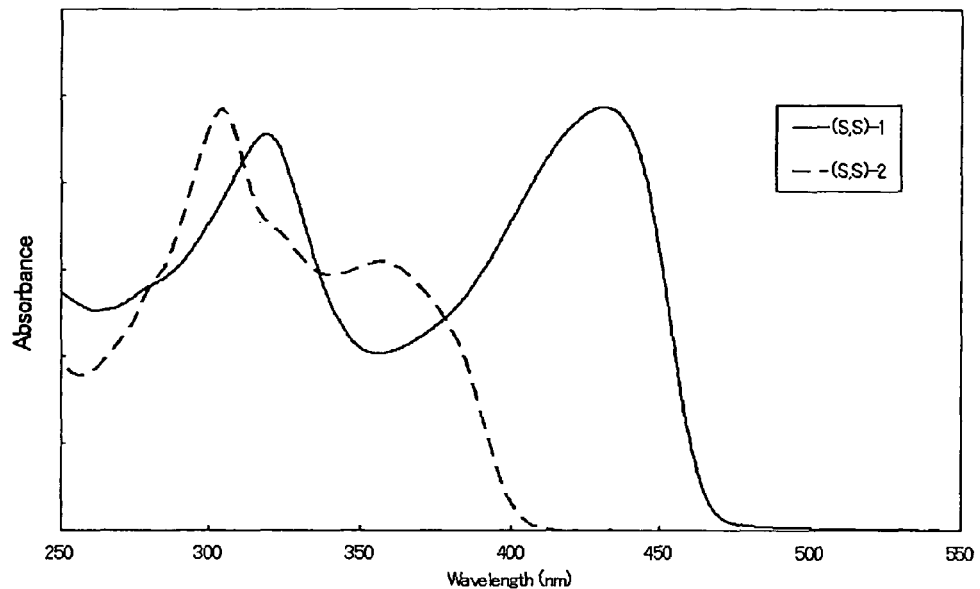
FIG. 1 is an ultraviolet and visible absorption spectrum of a variety of compounds.

The fluorescent molecular wire of the present invention is constituted by a fluorescent polymer main chain to which an optically active substituent having asymmetry recognition ability toward primary amines is linked so as to be a conjugatable form.

The term "fluorescent molecular wire" refers to a fluorescent polymer having a fluorescent polymer main chain in which the excitation energy can move freely within an effective conjugated chain. The fluorescent polymer main chain has a structure in which conjugated systems are linked together so that the excitation energy can move within the polymer main chain. Examples of such a fluorescent polymer main chain include a polyarylene structure, a poly(arylene ethynylene) structure, and a poly(arylene vinylene) structure, preferably, a polyphenylene structure, a polythiophene structure, a poly(phenylene thiophenylene) structure, a poly(phenylene ethynylene) structure, a poly(thiophenylene ethynylene) structure, or a poly(phenylene vinylene) structure. In the present invention, the polymer main chain is preferably a poly(phenylene ethynylene) structure or a poly(phenylene thiophenylene) structure, and more preferably a poly(phenylene ethynylene) structure.

The fluorescent polymer main chain may contain a substituent other than the optically active substituent in order to avoid steric hindrance due to the optically active substituents and improve the solubility. A case in which the optically active substituent is linked to a benzene ring of poly(phenylene ethynylene) will be described as an example. The benzene ring to which the optically active substituent is linked or a benzene ring adjacent to that benzene ring may contain, for example, an alkyl group, an alkoxy group, a di- or mono-alkylamide group, or an alkyl ester group. There is no particular limitation regarding the type, position, and number of such substituents other than the optically active substituent, as long as those substituents do not inhibit the fluorescence properties and the asymmetry recognition ability. A linear or branched alkyl group having 1 to 20 carbon atoms, an alkoxy group having 1 to 20 carbon atoms, a linear or branched di- or mono-alkylamide group having 1 to 20 carbon atoms, or a linear or branched alkyl ester group having 1 to 20 carbon atoms is preferable, and such a substituent may be incorporated in a benzene ring, for example.

In the present invention, the optically active substituent having asymmetry recognition ability toward primary amines is represented by the following formula (I):

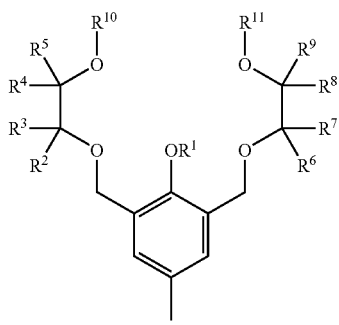

(I)

where $R^1$ represents a hydrogen atom or an alkyl group having 1 to 10 carbon atoms; $R^2$, $R^3$, $R^4$, $R^5$, $R^6$, $R^7$, $R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent; and $R^{10}$ and $R^{11}$ represent independently a hydrogen atom or an alkyl group having 1 to 15 carbon atoms that may have a heteroatom, and $R^{10}$ and $R^{11}$ may be bonded to form an alkylene group having 2 to 30 carbon atoms that may have a heteroatom.

$R^1$ represents a hydrogen atom or an alkyl group having 1 to 10 carbon atoms. Preferably, $R^1$ is a hydrogen atom and a methyl group.

$R^2$, $R^3$, $R^4$, $R^5$, $R^6$, $R^7$, $R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent. Here, examples of the substituent include a hydroxyl group, an alkoxy group having 1 to 10 carbon atoms, a thiol group, an amino group, a nitro group, and a halogen atom (e.g., a fluorine atom, a chlorine atom, a bromine atom, and an iodine atom).

Preferably, $R^2$, $R^3$, $R^4$, $R^6$, $R^7$, and $R^8$ are hydrogen atoms.

Examples of $R^5$ and $R^9$ include an aryl group having 6 to 30 carbon atoms, such as a phenyl group and a 1-naphthyl group, a cyclic alkyl group having 3 to 30 carbon atoms that may have a substituent, such as a 1-adamanthyl group. An aryl group having 6 to 12 carbon atoms or a cyclic alkyl group having 3 to 10 carbon atoms is preferable. More preferred examples of $R^5$ and $R^9$ include a phenyl group, a 1-naphthyl group, a 1-adamanthyl group, a 1-(3,5-dimethyl)phenyl group, and a 1-bi-2-naphthyl group, among which a phenyl group is preferable.

$R^{10}$ and $R^{11}$ represent independently a hydrogen atom or an alkyl group having 1 to 15 carbon atoms that may have a heteroatom, and $R^{10}$ and $R^{11}$ may be bonded to form an alkylene group having 2 to 30 carbon atoms that may have a substituent or may have a heteroatom. Here, examples of the heteroatom include an oxygen atom, a sulfur atom, and a nitrogen atom. Preferred $R^{10}$ and $R^{11}$ include a group formed by combining $R^{10}$ and $R^{11}$ and represented by the formula:

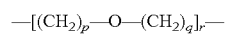

where p, q, and r represent independently an integer of 1 to 15. A pseudo-18-crown-6 type in which p and q are each 2 and r is 1 is more preferable. In which case, the optically active substituent is represented by the following formula (II):

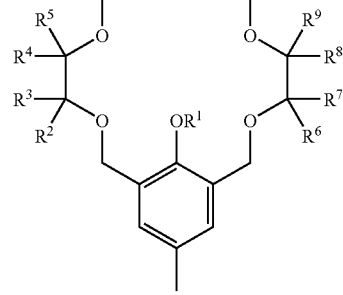

(I)

where $R^1$, $R^2$, $R^3$, $R^4$, $R^5$, $R^6$, $R^7$, $R^8$, and $R^9$ are defined as above.

The above-described optically active substituent is introduced directly into the polymer main chain of the fluorescent molecular wire as described above, or coupled thereto via a spacer. As the spacer, any group can be used as long as the optically active substituent is conjugated with the fluorescent polymer main chain and the excitation energy can move freely, and mono- or poly-arylene, mono- or poly-alkylene, mono- or poly-vinylene, or a combination thereof is preferable, and an ethynylene group is more preferable. By spacing the optically active substituent away from the polymer main chain via the spacer, steric congestion can be avoided.

Preferred examples of such a fluorescent molecular wire include a compound represented by formula (III):

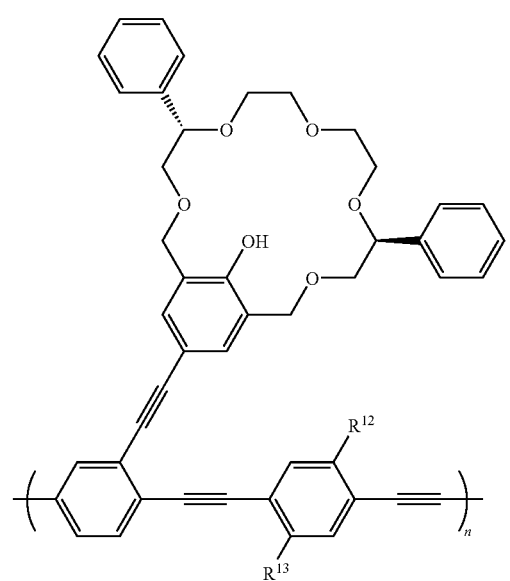

(III)

where $R^{12}$ and $R^{13}$ represent independently a hydrogen atom, an alkyl group having 1 to 20 carbon atoms, an alkoxy group having 1 to 20 carbon atoms, a di- or mono-alkylamide group having 1 to 20 carbon atoms, or an alkyl ester group having 1 to 20 carbon atoms; and n is an integer of 5 or more. The basic framework of the optically active substituent of the compound represented by this formula (III) is a phenolic pseudo-18-crown-6 type having two asymmetric carbon atoms. This optically active substituent is introduced into the polymer main chain of the fluorescent molecular wire at a para position to the phenolic hydroxy group via an ethynylene group. Thus, a high electron negativity of the sp carbon facilitates acid dissociation of the phenolic hydroxy group, and therefore amines can be captured effectively. $R^{12}$ and $R^{13}$, which are substituents other than the optically active substituent in the polymer main chain, are more preferably decyloxy groups, in which case the solubility of the polymer may be increased.

In the fluorescent molecular wire of the present invention, the optically active substituent (hereinafter sometimes referred to as the "receptor site") forms a complex selectively with either the R-form or the S-form of amines and amino acids and derivatives thereof In the present invention, there is no particular limitation regarding the amines and the amino acids and derivatives thereof Moreover, which of the R-form or the S-form of the amines and the amino acids and derivatives thereof can form a complex more effectively may depend on the stereostructure of the receptor site.

In the fluorescent molecular wire of the present invention, the formation of complex between the optically active substituent (receptor site) and a primary amine causes a charge transfer from the receptor site to the polymer main chain, which results in a quenching of the fluorescence. The mechanism of this quenching is the same as that of a conventional monomeric pseudo-18-crown-6 (see Japanese Laid-Open Patent Publication No. 2004-75624). However, the mechanism of signal amplification is entirely different in that in the monomeric pseudo-18-crown-6, apparent quenching may be amplified by the fact that the fluorescence emission band of the receptor site overlaps with the absorption band of a complex formed with the target, whereas in the fluorescent molecular wire of the present invention, quenching efficiency is increased by the mechanism shown in (B) of the above-described scheme. Moreover, quenching mechanisms that have been reported in connection with conventional fluorescent molecular wires are based on the interaction with acid or ion or the interaction between polymer chains (see Q. Zhou and T. M. Swager, ibid; K. B. Crawford et al., ibid; J.-S. Yang and T. M. Swager, ibid; and J. Kim et al., ibid). These mechanisms also are entirely different from the quenching mechanism of the fluorescent molecular wire of the present invention. Furthermore, the fluorescent molecular wire of the present invention also has an improved asymmetry recognition ability toward primary amines when compared to the monomer type.

There is no particular limitation regarding the method for producing the fluorescent molecular wire of the present invention. Generally, it can be obtained by polymerizing fluorescent monomer units into which a receptor site was introduced. For example, a fluorescent molecular wire represented by the formula (III) in which $R^{12}$ and $R^{13}$ are decyloxy groups can be obtained from (S)-mandelic acid ((S)-3) through a synthetic pathway described in the following scheme:

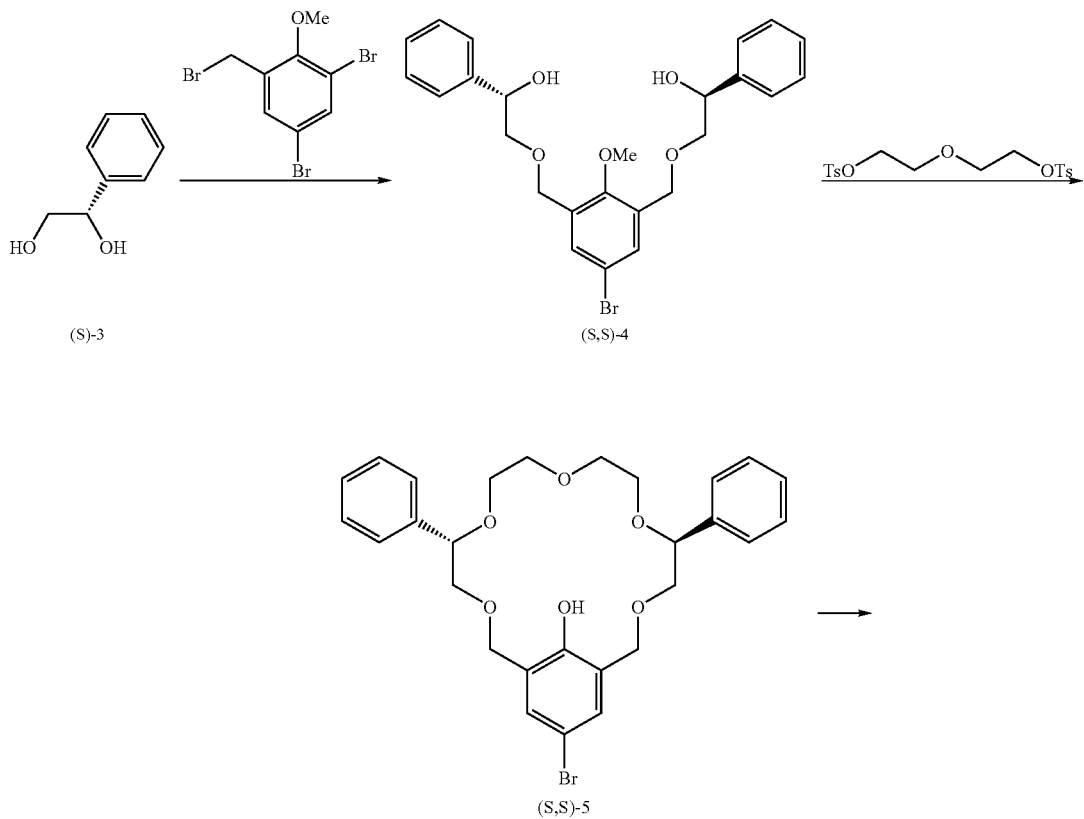

11
-continued
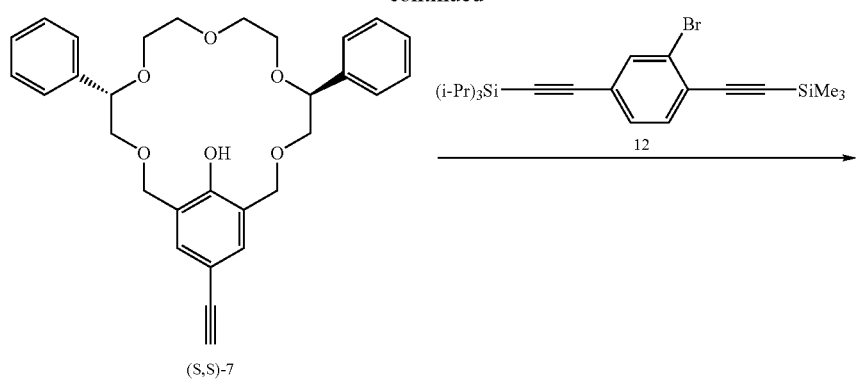
12
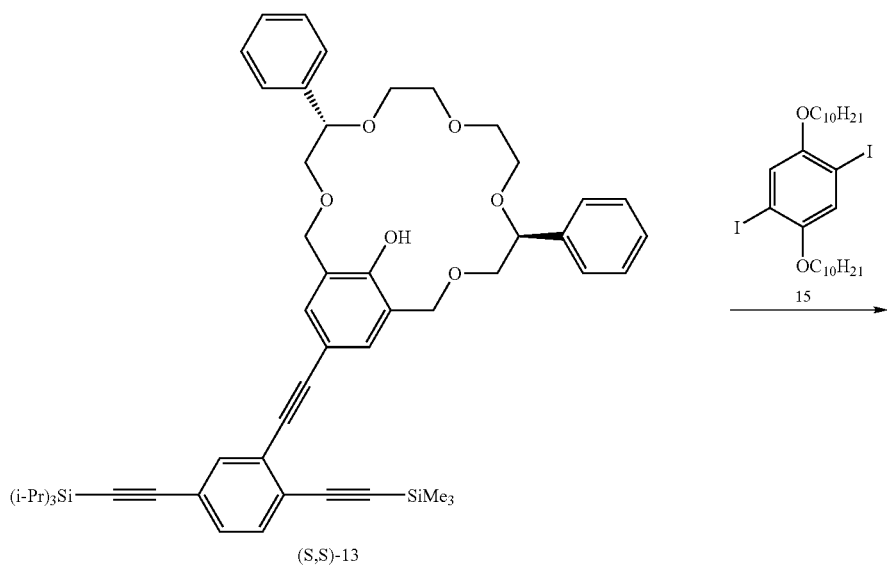
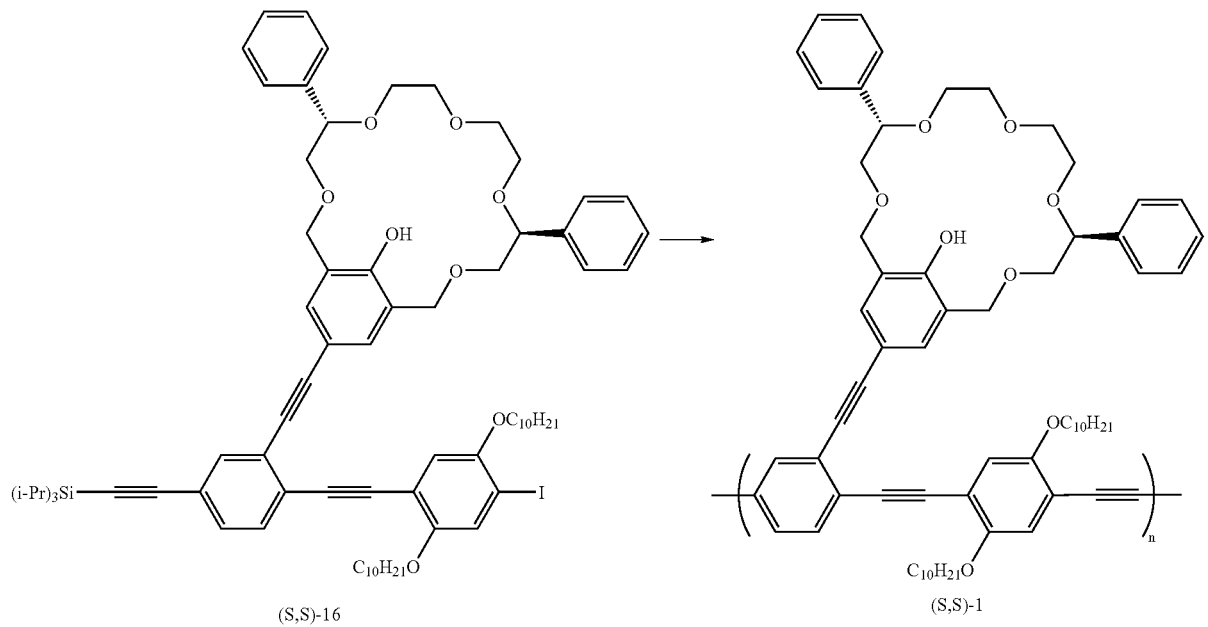

More specifically, the fluorescent molecular wire of the present invention can be produced by a method described in examples below. These examples are among embodiments of the present invention, and the present invention is not limited only to the examples below.

In this manner, the fluorescent molecular wire in which the optically active substituent represented by the formula (I) is linked to the fluorescent polymer main chain so as to be a conjugatable form can be obtained.

The chiral sensor of the present invention is constituted by the above-described fluorescent molecular wire. As the chiral sensor of the present invention, the above-described fluorescent molecular wire may be used without being subjected to any treatment or in a form in which it is dissolved in a solvent. Alternatively, it is possible that the above-described fluorescent molecular wire is mixed into a thermoplastic resin such as polyethylene, polypropylene, or polystyrene and the mixture is formed into a film such as a porous film or a product having desired shape and size, such as a bead, a pellet, or a plate. Thus, the chiral sensor of the present invention can be used in a variety of forms for a wide range of purposes.

The chiral sensor of the present invention is capable of recognizing asymmetry of primary amines with high sensitivity and high selectivity and thus is very useful for practical applications. For example, since amines, amino acids, and amino alcohols include a large amount of physiologically active substances, it can be preferably used for separation, sensing, sensing for detection of a narcotic drug or identification of the place of production, and the like.

EXAMPLES

In the examples below, the following analyzers were used:

(a) NMR spectrum: nuclear magnetic resonance spectrum JEOL JNM-GSX-270, AL-400, and Varian Mercury-300;

(b) IR spectrum: JASCO Fourier transform infrared spectrometer FT/IR-410;

(c) Optical rotation: JASCO digital polarimeter DIP-370;

(d) Melting point: a hot plate equipped with a microscope;

(e) Mass spectrum: JEOL JMS-DX303HF;

(f) LC mass spectrum: SHIMADZU LCMS-2010;

(g) Open column chromatography: MERCK Silica-gel 60 (70-230 mesh ASTM);

(h) Recycling preparative high-performance liquid column chromatography: LC-908 600×20 mm JAUGEL-1H, 2H GPC manufactured by Japan Analytical Industry Co., Ltd.;

(i) Thin layer chromatography: MERCK Silica-gel 60 $F_{254}$;

(j)) HPLC: HITACHI L7100, L7240, MightySil RP-18L 150-4.6, SHIMADZU LC-10AT, SPD-10A;

(k) Ultraviolet and visible absorption spectrum: HITACHI U-3310;

(l) Fluorescence emission spectrum: JASCO FP-6600.

Example 1

Synthesis of crown ether (S,S)-6

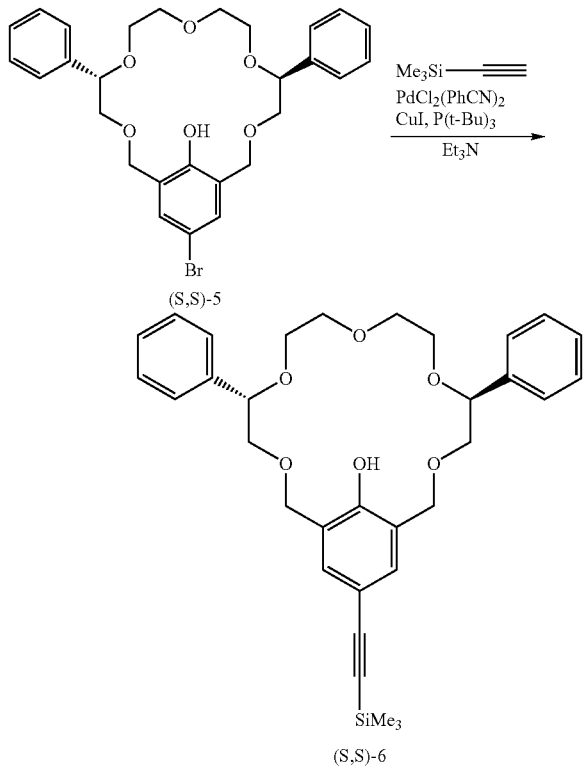

First, a 20 mL side-arm recovery flask was equipped with a septum, an Allihn condenser, and a magnetic stirrer and flame-dried under a nitrogen atmosphere. Then, copper (I) iodide (3.5 mg, 18 μmol) and dichlorobis(benzonitrile)palladium (II) ($PdCl_2(PhCN)_2$: 27.5 mg, 72.1 μmol) were placed into the flask and the atmosphere was replaced with argon. A solution of a crown ether (S,S)-5 (see Japanese Laid-Open Patent Publication No. 2004-75624) (414 mg, 762 μmol) in triethylamine (6.0 mL), which was previously degassed by argon bubbling, was added thereto, and further triethylamine (1.0 mL) was poured into the flask with washing. Then, tri-t-butylphosphine (20 μL, 74 μmol) and (trimethylsilyl)acetylene (150 μL, 1.06 μmol) were added thereto, and the mixture was stirred at 50° C. for 14 hours. The progress of the reaction was monitored by LC-MS. After adding 1 N hydrochloric acid, the reaction mixture was extracted with ether, and the organic layer was washed with saturated brine. The mixture obtained was dried over magnesium sulfate and concentrated, and thereafter the concentrate was purified by silica gal column chromatography (eluent: n-hexane/ethyl acetate=9/1) and then by recycling preparative HPLC, to give a crown ether (S,S)-6 (184 mg, 328 μmol) as a beige solid (yield: 43%). Moreover, the raw material (S,S)-5 (165 mg, 304 μmol) was recovered (yield: 40%).

Compound (S,S)-6: $^1$H NMR (270 MHz, $CDCl_3$) δ8.39 (s, 1H), 7.35-7.27 (m, 12H), 4.72 (s, 4H), 4.66 (dd, J=8.8, 3.1 Hz, 2H), 3.79-3.58 (m, 12H), 0.21 (s, 9H); $^{13}$C NMR (67.8 MHz, $CDCl_3$) δ156.2, 138.5, 133.2, 128.4, 127.9, 126.8, 124.6, 113.9, 105.1, 92.1, 81.4, 74.9, 70.6, 70.3, 68.9, 0.19; IR (KBr)

3346, 3061, 3029, 2955, 2898, 2866, 2150, 1607, 1480, 1453, 1096, 856, 701 cm$^{-1}$; MS (APCI) m/z 559 (M−H)$^-$.

Example 2

Synthesis of Crown Ether (S,S)-7

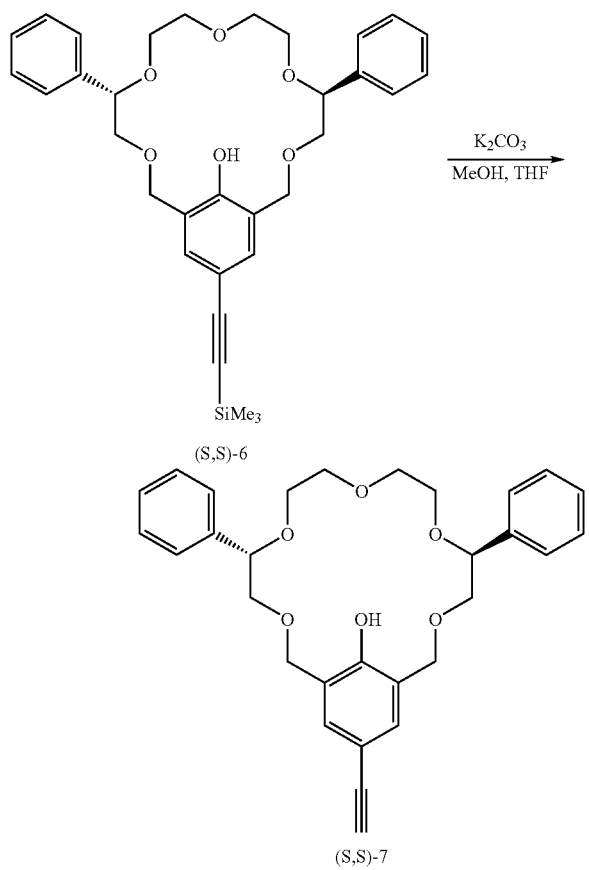

First, the crown ether (S,S)-6 (160 mg, 285 μmol), tetrahydrofuran (1.5 mL), methanol (2.0 mL), and potassium carbonate (89 mg, 650 μmol) were placed into a 20 mL recovery flask equipped with a calcium chloride tube and a magnetic stirrer, and the mixture was stirred at room temperature for 14 hours. The progress of the reaction was monitored by LC-MS. After adding water, the reaction mixture was extracted with ether, and the organic layer was washed with saturated brine. The mixture obtained was dried over magnesium sulfate and concentrated, and thereafter the concentrate was purified by silica gel column (eluent: n-hexane/ethyl acetate=4/1), to give a crown ether (S,S)-7 (130 mg, 266 μmol) as a beige solid (yield: 93%).

Compound (S,S)-7: $^1$H NMR (270 MHz, CDCl$_3$) δ 8.43 (s, 1H), 7.35-7.27 (m, 12H), 4.73 (s, 4H), 4.66 (dd, J=8.7, 2.3 Hz, 2H), 3.79-3.58 (m, 12H), 2.94 (s, 1H); $^{13}$C NMR (67.8 MHz, CDCl$_3$) δ 156.4, 138.5, 133.4, 128.4, 128.0, 126.8, 124.7, 112.7, 83.6, 81.4, 75.4, 75.0, 70.6, 70.3, 69.0; IR (KBr) 3337, 3292, 3060, 3029, 2905, 2866, 2104, 1608, 1480, 1452, 1266, 1094, 758, 701 cm$^{-1}$; MS (APCI) m/z 487 (M−H)$^-$.

Example 3

Synthesis of Compound 8

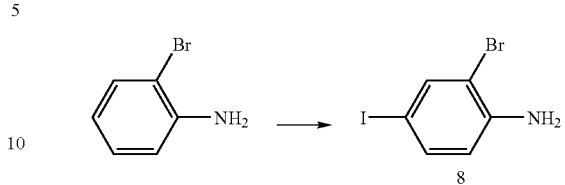

First, dichloromethane (108 mL) and methanol (43 mL) were placed into a 300 mL recovery flask that was equipped with a calcium chloride tube and a magnetic stirrer and that was shielded from light. Then, 2-bromoaniline (1.50 g, 8.55 mmol), BTMA ICl$_2$ (3.28 g, 9.42 mmol) (BTMA: benzyltrimethylammonium), and calcium carbonate were added thereto, and the mixture was stirred for 10 hours. The progress of the reaction was monitored by TLC. After the reaction mixture was filtrated and concentrated, an aqueous solution of saturated sodium thiosulfate was added thereto, and the mixture was extracted with ether. The organic layer was dried over anhydrous magnesium sulfate and concentrated, and the concentrate was purified by silica gel column chromatography (eluent: n-hexane/ethyl acetate=19/1). Recrystallization from n-hexane gave a compound 8 (1.90 g, 6.36 mmol) as a colorless needle crystal (yield: 74%).

Compound 8: melting point 82.0-82.5° C.; $^1$H NMR (270 MHz, CDCl$_3$, 30° C.) δ 7.67 (d, J=2.0 Hz, 1H), 7.34 (dd, J=8.4, 2.0 Hz, 1H), 6.52 (d, J=8.4 Hz, 1H), 4.10 (s, 2H); $^{13}$C NMR (75.5 MHz, CDCl$_3$, 30° C.) δ 143.6, 139.7, 136.7, 117.1, 109.9, 78.3; IR (KBr) 3399, 3299, 3178, 1623, 1576, 1471, 1385, 1290, 1030, 870, 814 cm$^{-1}$; MS (EI) m/z 297 (M)$^+$.

Example 4

Synthesis of Compound 9

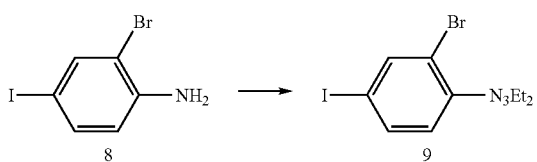

First, the compound 8 (500 mg, 1.68 mmol) and 5% hydrochloric acid (3.4 mL, 171 mg, 4.69 mmol) were placed into a 30 mL recovery flask equipped with a magnetic stirrer, and the mixture was stirred. The reaction mixture was cooled to 0° C. in an ice bath, and an aqueous solution (1.3 mL) of sodium nitrite (150 mg, 2.17 mmol) was added dropwise thereto. Then, potassium carbonate (549 mg, 3.97 mmol), water (8 mL), and diethylamine (320 μL, 224 mg, 3.06 mmol) were placed into another 30 mL recovery flask equipped with a magnetic stirrer, and the mixture was cooled to 0° C. in an ice bath. The previously obtained solution was added to this mixture with cooling to 0° C., and the resultant mixture was stirred for one hour. The reaction was monitored by TLC. The reaction mixture was extracted with ether, and the organic layer was washed with saturated brine. The mixture obtained was dried over anhydrous magnesium sulfate and concentrated, and thereafter the concentrate was purified by silica gel column chromatography (eluent: n-hexane), to give a compound 9 (565 mg, 1.48 mmol) as a yellowish-brown oily product (yield: 88%).

Compound 9: $^1$H NMR (270 MHz, CDCl$_3$, 30° C.) δ 7.88 (d, J=2.0 Hz, 1H), 7.50 (dd, J=8.5, 2.0 Hz, 1H), 7.13 (d, J=8.5 Hz, 1H), 3.78 (q, J=7.1 Hz, 4H), 1.30 (bs, 6H); $^{13}$C NMR (75.5 MHz, CDCl$_3$, 30° C.) δ 148.1, 140.5, 136.4, 120.5, 119.7, 88.3, 49.4, 42.3, 14.6, 11.0; IR (neat) 2973, 2932, 2870, 1544, 1457, 1408, 1338, 1248, 1201, 1109, 1035, 819, 590 cm$^{-1}$; MS (FAB) m/z 382 (M+H)$^+$.

Example 5

Synthesis of Compound 10

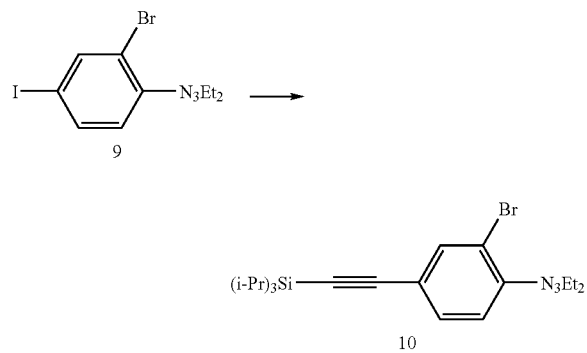

First, a 10 mL side-arm recovery flask was equipped with a septum, a Dimroth condenser, and a magnetic stirrer and flame-dried under a nitrogen atmosphere. Then, copper (I) iodide (18.9 mg, 96.3 μmol) and dichlorobis(triphenylphosphine)palladium (II) (PdCl$_2$(PPh$_3$)$_2$: 33.3 mg, 47.4 μmol) were placed into the flask and the atmosphere was replaced with argon. Then, a solution (5.4 mL) of the compound 9 (295 mg, 772 μmol) in triethylamine, which was previously degassed by argon bubbling, and (triisopropylsilyl)acetylene (200 μL, 934 μmol) were added thereto, and the mixture was stirred for 3 hours. The progress of the reaction was monitored by HPLC. After adding 1 N hydrochloric acid, the reaction mixture was extracted with ether, and the organic layer was washed with saturated brine. The mixture obtained was dried over anhydrous magnesium sulfate and concentrated, and thereafter the concentrate was purified by silica gel column chromatography (eluent: n-hexane), to give a compound 10 (259 mg, 593 μmol) as a yellow oily product (yield: 77%).

Compound 10: $^1$H NMR (270 MHz, CDCl$_3$, 30° C.) δ 7.68 (s, 1H), 7.32 (s, 2H), 3.79 (q, J=7.3 Hz, 4H), 1.31 (bs, 6H), 1.13 (bs, 21H); $^{13}$C NMR (75.5 MHz, CDCl$_3$, 30° C.) δ 148.1, 136.1, 131.2, 120.8, 119.1, 117.6, 106.0, 91.2, 49.4, 42.3, 19.4, 19.1, 18.9, 18.6, 18.4, 14.6, 12.0, 11.9, 11.6, 11.3, 11.2, 11.1; IR (neat) 2942, 2891, 2865, 2154, 1532, 1466, 1379, 1332, 1238, 1202, 1108, 1039, 996, 882, 828, 760, 677 cm$^{-1}$; MS (FAB) m/z 436 (M+H)$^+$.

Example 6

Synthesis of Compound 11

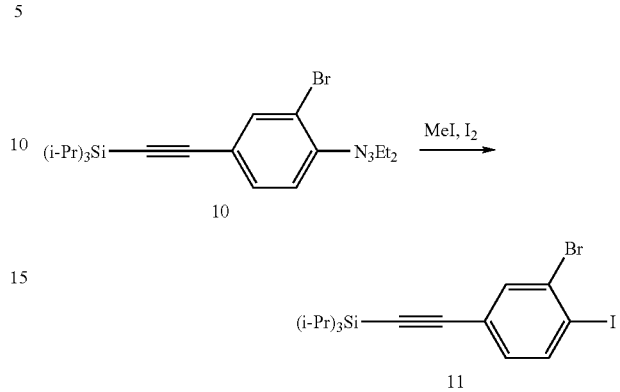

First, the compound 10 (8.15 g, 18.7 mmol), methyl iodide (50.0 mL, 110 g, 799 mmol), and iodine (4.85 g, 19.1 mmol) were placed into a pressure-resistant glass tube, and the tube was degassed by argon bubbling, sealed tightly and heated at 100° C. for 12 hours. After opening the tube, the reaction mixture was extracted with ether, and the organic layer was washed with an aqueous solution of saturated sodium thiosulfate and then with saturated brine. The mixture obtained was dried over magnesium sulfate and concentrated, and thereafter the concentrate was passed through a silica gel column (eluent: n-hexane), to give a compound 11 (7.09 mg, 15.3 mmol) as a pale yellow oily product (yield: 82%).

Compound 11: $^1$H NMR (270 MHz, CDCl$_3$) δ 7.78 (d, J=8.2 Hz, 1H), 7.70 (d, J=2.0 Hz, 1H), 7.06 (dd, J=8.2, 2.0 Hz, 1H), 1.12 (s, 21H); $^{13}$C NMR (67.8 MHz, CDCl$_3$) δ 139.8, 135.4, 131.5, 129.3, 125.0, 104.4, 101.0, 93.9, 18.7, 11.4; IR (neat) 2942, 2890, 2865, 2160, 1574, 1522, 1462, 1448, 1006, 882, 865, 818, 695, 677, 661 cm$^{-1}$; MS (FAB) m/z 463 (M+H)$^+$.

Example 7

Synthesis of Compound 12

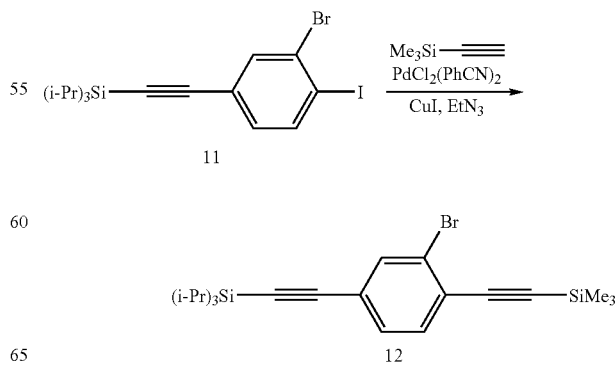

First, a 5 mL side-arm recovery flask was equipped with a septum, an Allihn condenser, and a magnetic stirrer and flame-dried with heat gun under a nitrogen atmosphere. Then, copper (I) iodide (5.4 mg, 28 μmol) and PdCl$_2$(PPh$_3$)$_2$ (6.3 mg, 9.0 μmol) were placed into the flask and the atmosphere was replaced with argon. A solution (1.5 mL) of the compound 11 (75.5 mg, 163 μmol) in triethylamine, which was previously degassed by argon bubbling, was added thereto, and further (trimethylsilyl)acetylene (48 μL, 33 mg, 340 μmol) was added, and then the mixture was stirred at room temperature for one hour. The progress of the reaction was monitored by HPLC. After adding 1 N hydrochloric acid, the reaction mixture was extracted with ether, and the organic layer was washed with saturated brine. The mixture obtained was dried over magnesium sulfate, and after the catalyst was removed using a filtration column (eluent: n-hexane), was purified by recycling preparative HPLC, to give a compound 12 (67.6 mg, 156 μmol) as a pale yellow liquid (yield: 96%).

Compound 12: $^1$H NMR (270 MHz, CDCl$_3$) δ 7.66 (d, J=1.5 Hz, 1H), 7.39 (d, J=8.0 Hz, 1H), 7.31 (dd, J=8.0, 1.5 Hz, 1H), 1.12 (s, 21H), 0.27 (s, 9H); $^{13}$C NMR (67.8 MHz, CDCl$_3$) δ 135.3, 132.9, 130.3, 125.2, 125.0, 124.8, 104.9, 102.7, 101.5, 94.4, 18.7, 11.4, −0.1; IR (neat) 2942, 2891, 2865, 2154, 2063, 1532, 1466, 1411, 1379, 1332, 1259, 1238, 1202, 1108, 882, 862, 760, 692, 676, 661 cm$^{-1}$; MS (FAB) m/z 433 (M+H)$^+$.

Example 8

Synthesis of Compound (S,S)-13

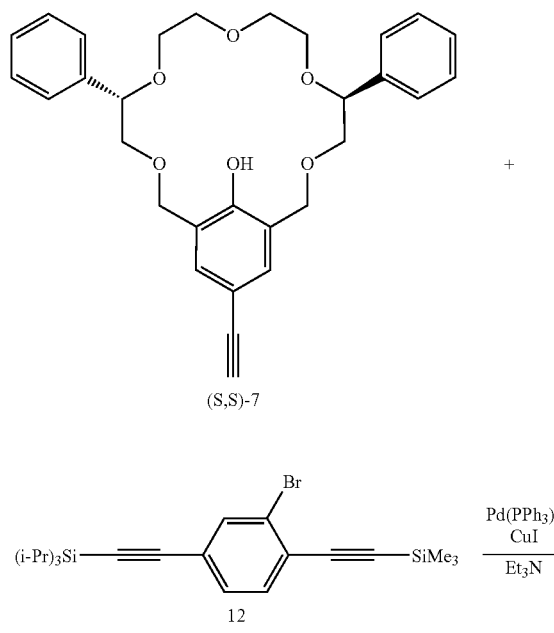

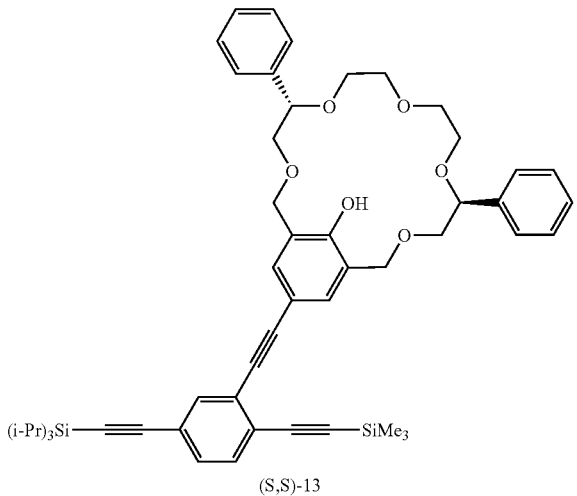

First, a 100 mL three-neck flask was equipped with a septum, a Dimroth condenser, a ball stopper, and a magnetic stirrer and flame-dried under a nitrogen atmosphere. Then, copper (I) iodide (35.3 mg, 180 μmol) and PdCl$_2$(PhCN)$_2$ (62.4 mg, 164 μmol) were placed into the flask and the atmosphere was replaced with argon. A solution of the compound 12 (759 mg, 1.75 mmol) in triethylamine (10.0 mL), which was previously degassed by argon bubbling, was added thereto, and further triethylamine (5.0 mL) was poured into the flask with washing. Then, tri-t-butylphosphine (100 μL, 369 mmol) was added thereto, and the mixture was heated to 50° C. in an oil bath. A solution of the crown ether (S,S)-7 (889 mg, 1.82 mmol) in triethylamine (25.0 mL), which was previously degassed by argon bubbling, was added thereto, and furthermore triethylamine (5.0 mL) was poured into the flask with washing. The resultant mixture was stirred at 50° C. for 3 hours. The progress of the reaction was monitored by TLC. After adding 1 N hydrochloric acid, the reaction mixture was extracted with ether, and the organic layer was washed with saturated brine. The mixture obtained was dried over anhydrous magnesium sulfate and concentrated, and thereafter the concentrate was purified by silica gel column chromatography (eluent: n-hexane/ethyl acetate=9/1→2/1), to give a compound (S,S)-13 (1.19 g, 1.41 mmol) as a beige solid (yield: 81%).

Compound (S,S)-13: melting point 52-54° C.; $^1$H NMR (270 MHz, CDCl$_3$) δ 8.44 (s, 1H), 7.56 (dd, J=1.6, 0.5 Hz, 1H), 7.40-7.26 (m, 12H), 7.39 (dd, J=8.0, 0.5 Hz, 1H), 7.29 (dd, J=8.0, 1.6 Hz, 1H), 4.75 (s, 4H), 4.67 (dd, J=8.9, 2.9 Hz, 2H), 3.79-3.54 (m, 12H), 1.12 (s, 21H), 0.24 (s, 9H); $^{13}$C NMR (67.8 MHz, CDCl$_3$) δ 156.3, 138.4, 134.7, 133.2, 132.0, 130.6, 128.5, 128.0, 126.8, 126.5, 124.9, 123.4, 113.8, 105.8, 103.3, 100.1, 94.0, 93.2, 86.1, 81.4, 74.9, 70.6, 70.4, 68.8, 18.7, 11.4, 0.2; IR (KBr) 3352, 3062, 3030, 2943, 2893, 2865, 2213, 2156, 1608, 1591, 1487, 1454, 1250, 1094, 859, 702 cm$^{-1}$; MS (FAB) m/z 863 (M+Na)$^+$.

Example 9

Synthesis of Compound (S,S)-14

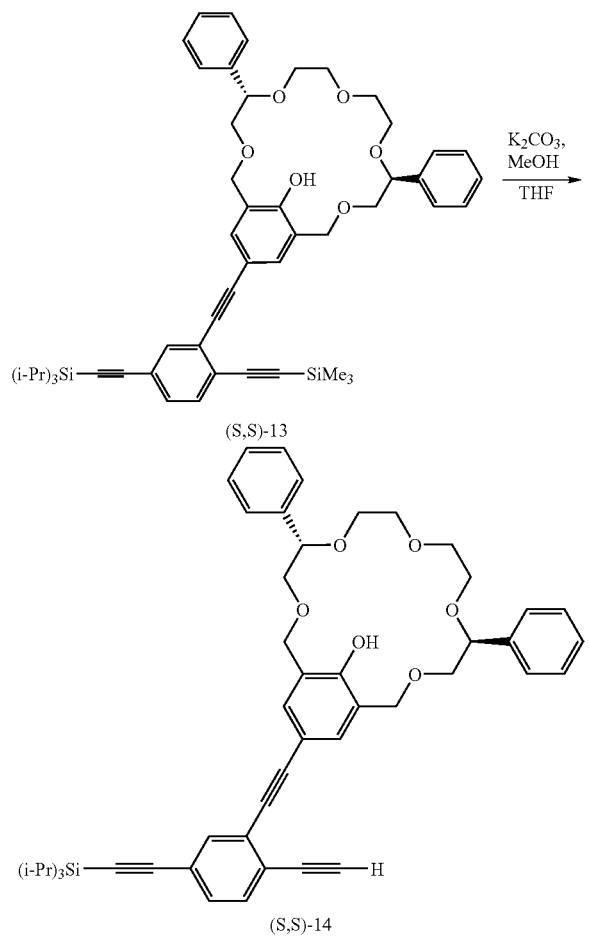

First, the crown ether (S,S)-13 (130 mg, 155 μmol), tetrahydrofuran (1.0 mL), methanol (500 μL), and potassium carbonate (50.2 mg, 361 μmol) were placed into a 20 mL recovery flask equipped with a calcium chloride tube and a magnetic stirrer, and the mixture was stirred at room temperature for 30 minutes. The progress of the reaction was monitored by TLC. After adding water, the reaction mixture was extracted with ether, and the organic layer was washed with saturated brine. The mixture obtained was dried over magnesium sulfate and concentrated, to give a compound (S,S)-14 (130 mg, 266 μmol) as a beige solid (yield: 93%).

Compound (S,S)-14: melting point 51-52° C.; $^1$H NMR (270 MHz, CDCl$_3$) δ 8.46 (s, 1H), 7.58 (d, J=1.7 Hz, 1H), 7.42 (d, J=7.9 Hz, 1H), 7.38-7.27 (m, 13H), 4.76 (s, 4H), 4.67 (dd, J=8.6, 2.9 Hz, 2H), 3.82-3.55 (m, 12H), 3.40 (s, 1H), 1.13 (s, 21H); $^{13}$C NMR (67.8 MHz, CDCl$_3$) δ 156.4, 138.5, 134.9, 133.1, 132.3, 130.7, 128.4, 128.0, 126.82, 126.77, 124.8, 123.8, 113.6, 105.7, 94.2, 93.4, 85.7, 82.1, 81.4, 75.0, 70.6, 70.4, 69.0, 18.7, 11.4; IR (KBr) 3344, 2942, 2864, 2212, 2153, 1591, 1537, 1488, 1453, 1344, 1329, 1265, 1245, 1094, 884, 756, 744, 702 cm$^{-1}$; MS (FAB) m/z 791 (M+Na)$^+$.

Example 10

Synthesis of Compound (S,S)-16

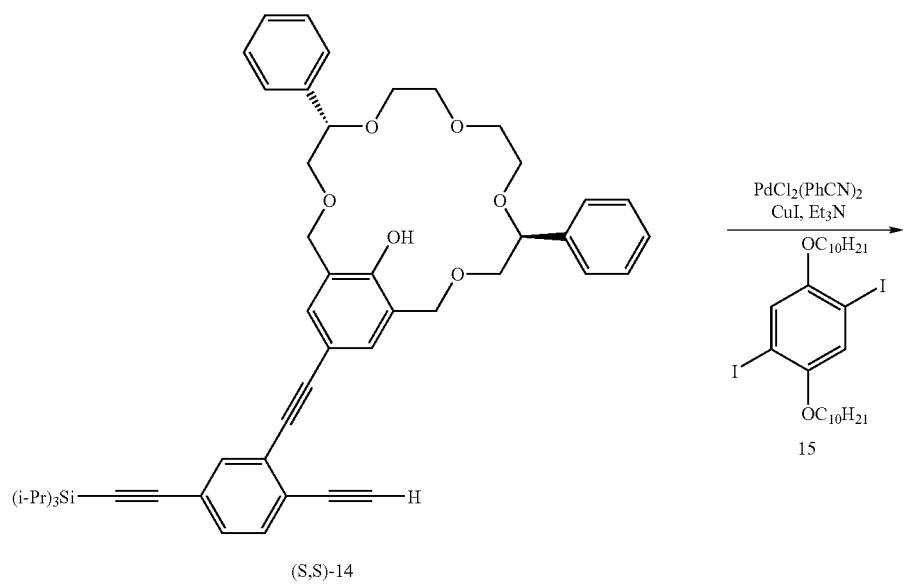

-continued

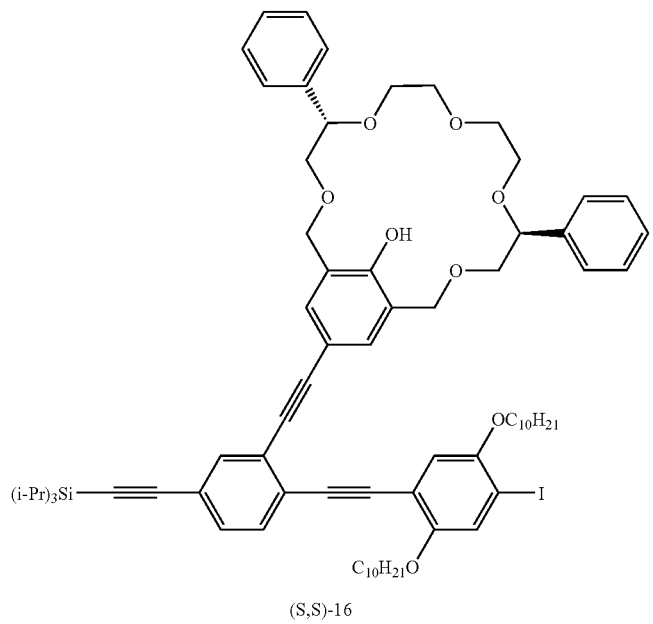

(S,S)-16

First, a 5 mL side-arm flask was equipped with a septum, a Dimroth condenser, and a magnetic stirrer and flame-dried under a nitrogen atmosphere. Then, copper (I) iodide (1.87 mg, 9.52 μmol), PdCl$_2$(PhCN)$_2$ (2.09 mg, 2.98 μmol), and a compound 15 (167 mg, 1260 mmol) were placed into the flask and the atmosphere was replaced with argon. Then, triethylamine (1.0 mL) previously degassed by argon bubbling was added thereto, and a solution of a crown ether (S,S)-22 (104 mg, 135 μmol) in triethylamine (0.5 mL) was added to the mixture dropwise using a syringe for 15 minutes. After the dropping was finished, the syringe was washed with triethylamine (0.3 mL), which was dropped, and thereafter the resultant mixture was stirred at room temperature for one hour. The progress of the reaction was monitored by TLC. After adding 2 N hydrochloric acid, the reaction mixture was extracted with ether, and the organic layer was washed with saturated brine. The mixture obtained was dried over anhydrous magnesium sulfate and concentrated, and thereafter the concentrate was purified by silica gel column chromatography (eluent: n-hexane/ethyl acetate=9/1), to give a compound (S,S)-16 (92.1 mg, 71.8 μmol) as a brown oily product (yield: 53%).

Compound (S,S)-16: $^1$H NMR (270 MHz, CDCl$_3$) δ 8.46 (s, 1H), 7.60 (d, J=1.5 Hz, 1H), 7.44 (d, J=8.1 Hz, 1H), 7.40-7.24 (m, 14H), 6.90 (s, 1H), 4.68-4.64 (m, 6H), 3.90 (t, J=6.3 Hz, 2H), 3.82-3.59 (m, 14H), 1.73-1.65 (m, 4H), 1.43-1.21 (m, 28H), 1.13 (s, 21H), 0.90-0.84 (m, 6H); $^{13}$C NMR (67.8 MHz, CDCl$_3$) δ 156.4, 154.3, 151.8, 138.4, 133.1, 131.2, 130.6, 128.4, 127.9, 126.8, 126.3, 125.4, 124.7, 124.2, 123.1, 116.0, 113.69, 113.66, 105.9, 94.4, 93.1, 92.9, 91.3, 87.9, 86.3, 81.3, 75.0, 70.5, 70.3, 70.1, 70.0, 69.0, 32.0, 31.9, 29.64, 29.61, 29.56, 29.40, 29.37, 29.25, 29.23, 26.2, 26.0, 22.7, 18.7, 14.2, 11.4; IR (neat) 3345, 2925, 2863, 2208, 2152, 1592, 1532, 1493, 1464, 1379, 1265, 1214, 1092, 1016, 910, 884, 757, 733, 701 cm$^{-1}$; MS (FAB) m/z 1306 (M+Na)$^+$.

Example 11

Synthesis of Monomer Unit (S,S)-17

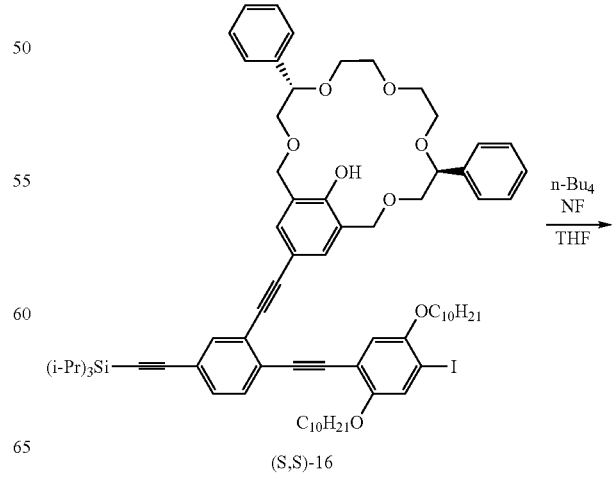

(S,S)-16

-continued

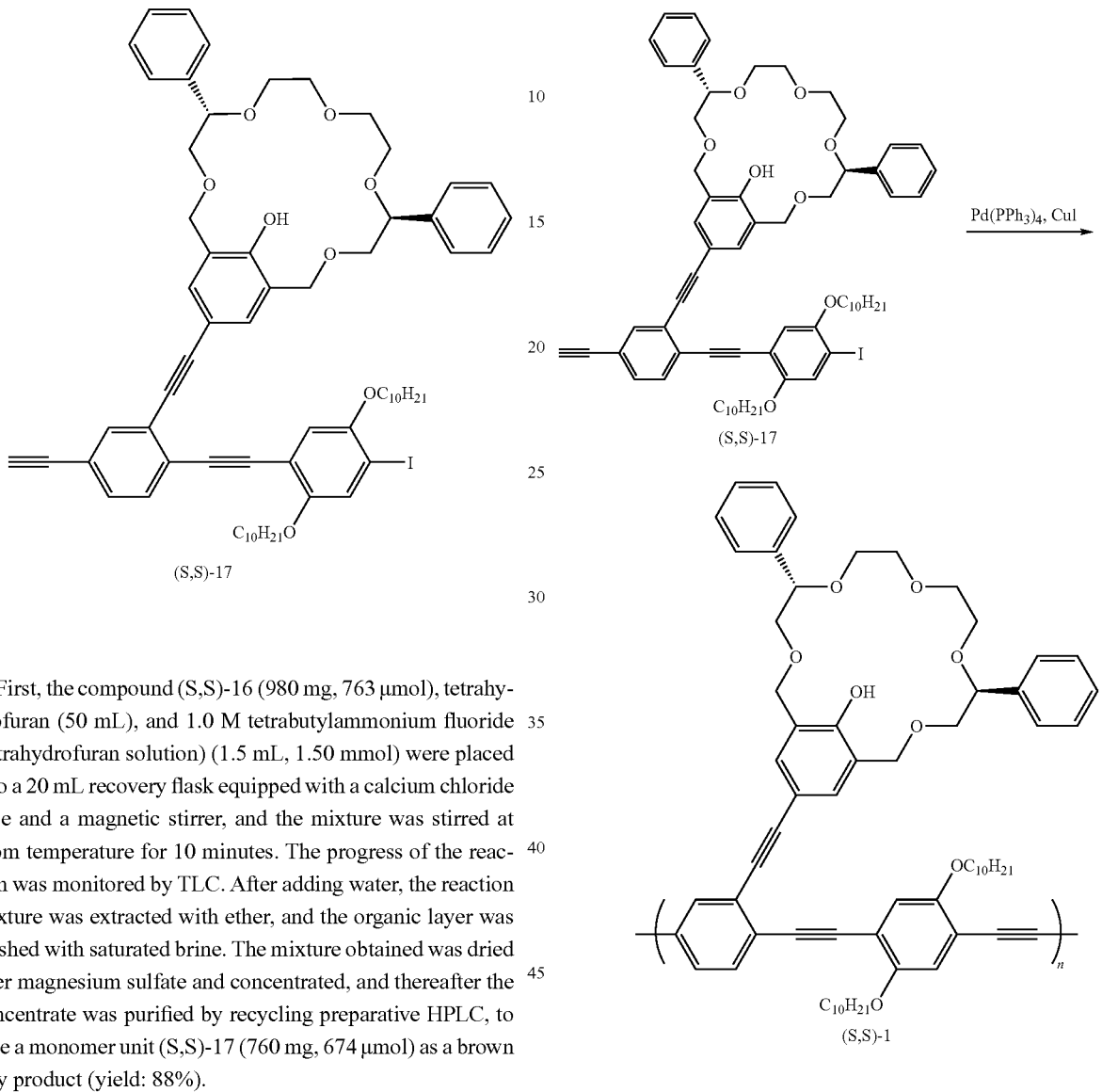

First, the compound (S,S)-16 (980 mg, 763 μmol), tetrahydrofuran (50 mL), and 1.0 M tetrabutylammonium fluoride (tetrahydrofuran solution) (1.5 mL, 1.50 mmol) were placed into a 20 mL recovery flask equipped with a calcium chloride tube and a magnetic stirrer, and the mixture was stirred at room temperature for 10 minutes. The progress of the reaction was monitored by TLC. After adding water, the reaction mixture was extracted with ether, and the organic layer was washed with saturated brine. The mixture obtained was dried over magnesium sulfate and concentrated, and thereafter the concentrate was purified by recycling preparative HPLC, to give a monomer unit (S,S)-17 (760 mg, 674 μmol) as a brown oily product (yield: 88%).

Compound (S,S)-17: $^1$H NMR (400 MHz, CDCl$_3$) δ 8.48 (s, 1H), 7.60 (d, J=1.5 Hz, 1H), 7.45 (d, J=8.2 Hz, 1H), 7.42-7.24 (m, 14H), 6.89 (s, 1H), 4.67-4.65 (m, 6H), 3.90 (t, J=6.5 Hz, 2H), 3.81-3.56 (m, 14H), 3.16 (s, 1H), 1.76-1.64 (m, 4H), 1.47-1.12 (m, 28H), 0.89-0.85 (m, 6H); $^{13}$C NMR (100 MHz, CDCl$_3$) δ 156.5, 154.3, 151.8, 138.4, 133.1, 131.4, 130.8, 128.5, 128.0, 126.8, 126.5, 126.0, 124.7, 124.2, 121.8, 116.1, 113.7, 113.6, 94.6, 92.7, 91.5, 88.0, 86.1, 82.6, 81.3, 79.1, 75.1, 70.5, 70.3, 70.2, 70.0, 68.9, 65.8, 32.0, 31.9, 29.65, 29.63, 29.62, 29.58, 29.41, 29.38, 29.2, 26.2, 26.0, 22.7, 14.2; IR (neat) 3304, 2925, 2855, 2207, 1593, 1534, 1492, 1465, 1378, 1264, 1213, 1094, 757, 701 cm$^{-1}$; MS (FAB) m/z 1150 (M+Na)$^+$.

Example 12

Synthesis of Molecular Wire (S,S)-1

First, a 50 mL three-neck flask was equipped with a septum, a ball stopper, a Dimroth condenser, and a magnetic stirrer and flame-dried with heat gun under a nitrogen atmosphere. Then, copper (I) iodide (11.6 mg, 59.1 μmol) and tetrakis(triphenylphosphine) palladium (0) (Pd(PPh$_3$)$_4$: 53.0 mg, 45.9 μmol) were placed into the flask and the atmosphere was replaced with argon. Then, a solution of the monomer unit (S,S)-17 (561 mg, 498 μmol) in diisopropylamine/toluene (v/v=7/3, 40.0 mL), which was previously degassed by argon bubbling, was added thereto, and the mixture was heated to 50° C. in an oil bath and stirred for 20 hours. After the reaction was finished, 2 N hydrochloric acid was added to the reaction mixture, and the mixture was extracted with chloroform, and then the organic layer was washed with saturated brine. The mixture obtained was dried over anhydrous magnesium sulfate and concentrated, and thereafter the concentrate was purified by recycling preparative HPLC, to give a molecular wire (S,S)-1 (450 mg) as an orange solid (yield: 91%).

Comparative Example 1

Synthesis of Compound (S,S)-19

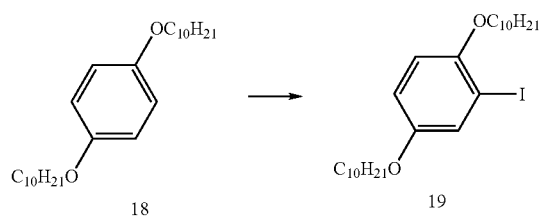

First, a 30 mL side-arm recovery flask was equipped with a septum, a Dimroth condenser, and a magnetic stirrer. Then, a compound 18 (1.50 g, 2.34 mmol) was placed into the flask, and the atmosphere was replaced with argon. Tetrahydrofuran (16 mL) was added thereto, and the mixture was cooled to −76° C. in a carbon dioxide-ethanol bath. Then, 1.6 M n-butyllithium (hexane solution) (1.8 mL, 2.88 mmol) was added thereto dropwise for 10 minutes, and the mixture was stirred with cooling for 2 hours and 30 minutes. The reaction was monitored by HPLC. After the reaction mixture was warmed to room temperature, an aqueous solution of saturated ammonium chloride was added thereto, the mixture was extracted with ether, and the organic layer was washed with saturated brine. The mixture obtained was dried over anhydrous magnesium sulfate and concentrated, and thereafter the concentrate was purified by silica gel column chromatography (eluent: n-hexane) and then by recycling preparative HPLC, to give a compound 19 (229 mg, 1.28 mmol) as a colorless oily product (yield: 55%).

Compound 19: $^1$H NMR (270 MHz, CDCl$_3$, 30° C.) δ 7.32 (d, J=3.0 Hz, 1H), 6.82 (dd, J=8.9, 3.0 Hz, 2H), 6.71 (d, J=8.9 Hz, 1H), 3.92 (t, J=6.6 Hz, 2H), 3.87 (t, J=6.6 Hz, 2H), 1.84-1.68 (m, 4H), 1.53-1.27 (m, 28H), 0.88 (t, J=6.9 Hz, 6H); $^{13}$C NMR (67.9 MHz, CDCl$_3$, 30° C.) δ 153.69, 152.07, 125.32, 115.36, 113.09, 87.00, 70.24, 68.89, 31.99, 31.96, 29.66, 29.63, 29.44, 29.42, 29.38, 26.19, 26.09, 22.76, 14.19.

Comparative Example 2

Synthesis of Compound (S,S)-20

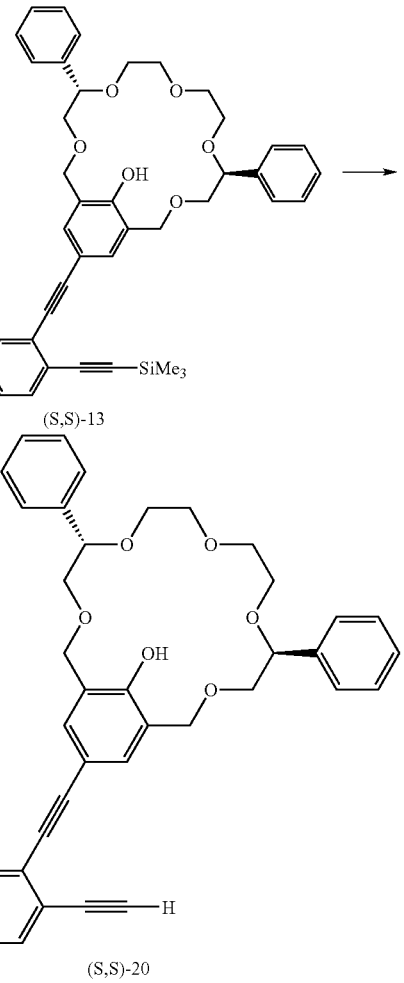

First, the compound (S,S)-13 (539 mg, 641 μmol), tetrahydrofuran (22 mL), and 1.0 M tetrabutylammonium fluoride (tetrahydrofuran solution) (2.8 mL, 2.80 mmol) were placed into a 50 mL recovery flask equipped with a calcium chloride tube and a magnetic stirrer, and the mixture was stirred for 45 minutes. The reaction was monitored by TLC. After adding 1 N hydrochloric acid, the reaction mixture was extracted with ether, and the organic layer was washed with saturated brine. The mixture obtained was dried over anhydrous magnesium sulfate and concentrated, and thereafter the concentrate was purified by silica gel column chromatography (eluent: n-hexane/ethyl acetate=4/1→3/1), to give a compound (S,S)-20 (349 mg, 570 μmol) as a white solid (yield: 89%).

Compound (S,S)-20: melting point 54.5-56.0° C.; $^1$H NMR (270 MHz, CDCl$_3$, 30° C.) δ 8.47 (s, 1H), 7.60 (d, J=1.3Hz, 1H), 7.44, (d, J=7.9Hz, 1H), 7.39-7.27 (m, 13H), 4.76 (s, 4H), 4.67 (dd, J=8.4, 3.0 Hz, 2H), 3.82-3.57 (m, 12H), 3.41 (s, 1H), 3.12 (s, 1H); $^{13}$C NMR (67.9 MHz, CDCl$_3$, 30° C.) δ 156.6, 138.5, 134.9, 133.1, 132.4, 130.7, 128.5, 128.0, 126.9, 126.8, 124.9, 124.5, 122.4, 113.5, 94.4, 85.5, 82.7, 82.4, 81.9, 81.4, 79.3, 75.1, 70.6, 70.4, 69.0.

Comparative Example 3

Synthesis of Compound (S,S)-2

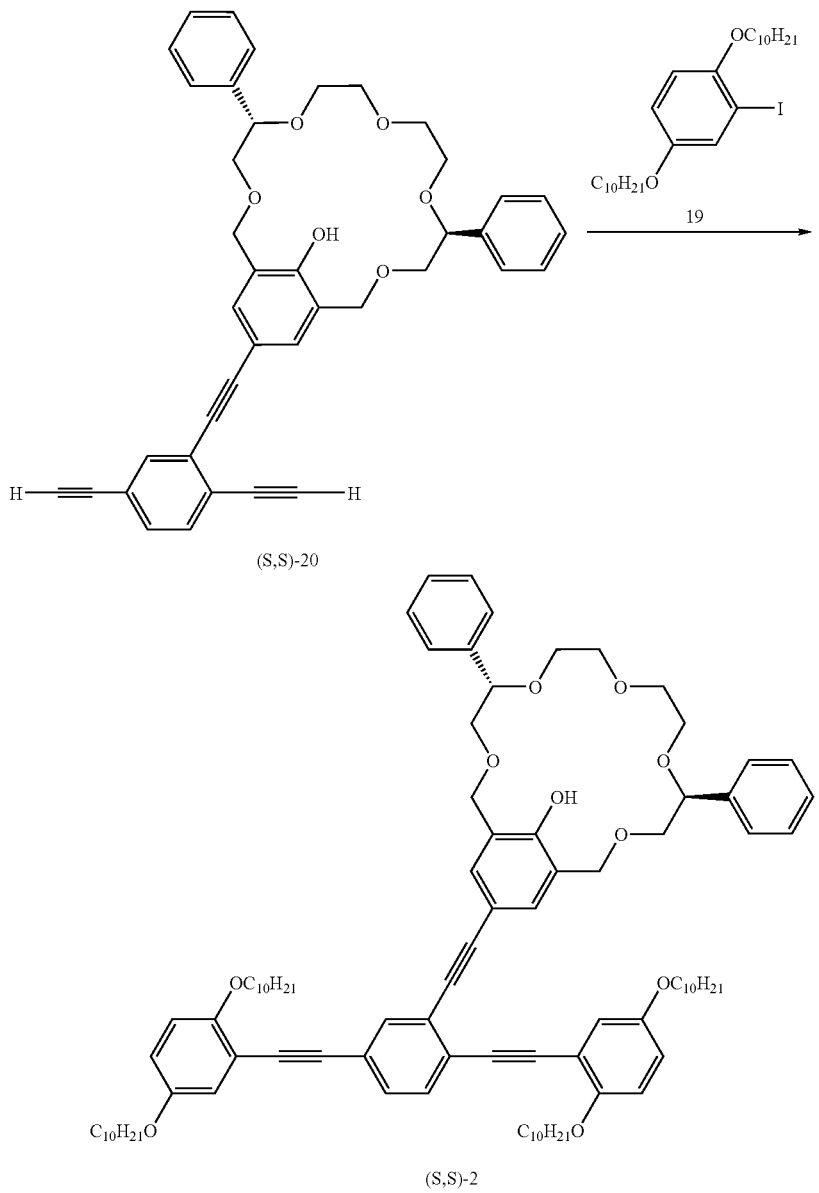

First, a 30 mL side-arm recovery flask was equipped with a septum, a Dimroth condenser, and a magnetic stirrer and flame-dried under a nitrogen atmosphere. Then, copper (I) iodide (17.5 mg, 91.4 μmol) and Pd(PPh$_3$)$_4$ (60.2 mg, 52.1 μmol) were placed into the flask and the atmosphere was replaced with argon. Triethylamine (1 mL) previously degassed by argon bubbling was added thereto. Then, a solution of the compound 19 (501 mg, 969 μmol) in triethylamine (720 μL), which was previously degassed by argon bubbling, was added thereto, and the mixture was washed with triethylamine (1.28 mL). Furthermore, a solution of the compound (S,S)-20 (260 mg, 424 μmol) in triethylamine (3 mL), which was previously degassed by argon bubbling, was added thereto, and the mixture was washed with additional triethylamine (4 mL) and stirred for 2 hours and 30 minutes. The reaction was monitored by TLC. After adding 1 N hydrochloric acid, the reaction mixture was extracted with ether, and the organic layer was washed with saturated brine. The mixture obtained was dried over anhydrous magnesium sulfate and concentrated, and thereafter the concentrate was purified by silica gel column chromatography (eluent: n-hexane/ethyl acetate=4/1) and then by recycling preparative HPLC, to give a compound (S,S)-2 (437 mg, 314 μmol) as a yellowish white solid (yield: 74%).

Compound (S,S)-2: melting point 39.0-39.5° C.; $^1$H NMR (400 MHz, CDCl$_3$, 30° C.) δ 8.42 (s, 1H), 7.64 (d, J=1.5 Hz, 1H), 7.48 (d, J=8.1 Hz, 1H), 7.39-7.26 (m, 13H), 7.04 (d, J=2.7 Hz, 1H), 7.00 (d, J=2.7 Hz, 1H), 6.86-6.76 (m, 4H), 4.69 (d, J=11.2 Hz, 2H), 4.67 (d, J=11.2 Hz, 2H), 4.65 (dd, J=8.9, 2.7 Hz, 2H), 4.03-3.56 (m, 20H), 1.87-1.65 (m, 8H), 1.53-1.21 (m, 56H), 0.90-0.83 (m, 12H); $^{13}$C NMR (101 MHz, CDCl$_3$, 30° C.) δ 156.43, 154.13, 152.80, 152.77, 138.56, 134.00, 133.23, 131.53, 130.24, 128.44, 127.95, 126.80, 126.35, 125.44, 124.70, 123.26, 118.59, 118.40, 116.89, 116.70, 114.51, 114.20, 113.93, 113.88, 113.38, 94.25, 92.38, 92.12, 91.68, 88.12, 86.50, 81.39, 75.05, 70.57, 70.44, 70.11, 69.91, 69.00, 68.78, 68.67, 31.96, 31.94, 29.70, 29.66, 29.63, 29.61, 29.48, 29.44, 29.41, 29.38, 26.15, 26.11, 26.09, 22.75, 22.73, 14.19, 14.17.

Example 18

Evaluation of Complex Forming Ability and Fluorescence Quenching Ability

The ultraviolet and visible absorption spectra of the fluorescent molecular wire (S,S)-1 and the comparative compound (S,S)-2 were measured in methylene chloride (FIG. 1). In (S,S)-1, the peak at 319 nm is due to absorption of the phenolic moiety and the peak at 431 nm is due to absorption of the poly(phenylene ethynylene) main chain. As for (S,S)-2, absorption of the phenolic moiety and absorption of the bis (phenylethynyl)benzene moiety are exhibited at 305 nm and 357 nm, respectively.

Figure 2:
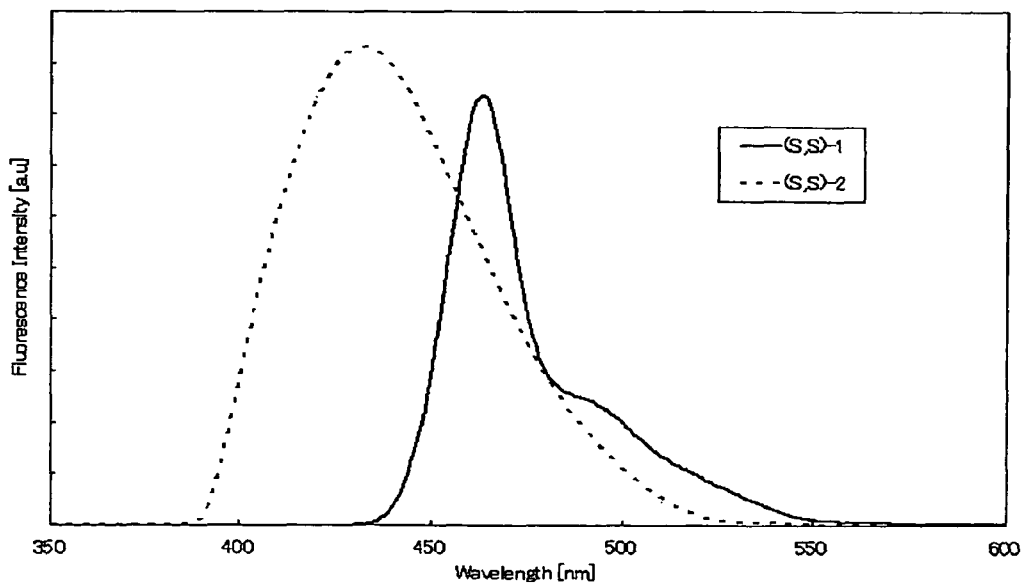
FIG. 2 is a fluorescence spectrum of a variety of compounds.

Then, the fluorescence spectra of (S,S)-1 and (S,S)-2 were measured in methylene chloride (FIG. 2). The fluorescence maximum wavelength was 463 nm for (S,S)-1 and 432 nm for (S,S)-2.

Figure 3:
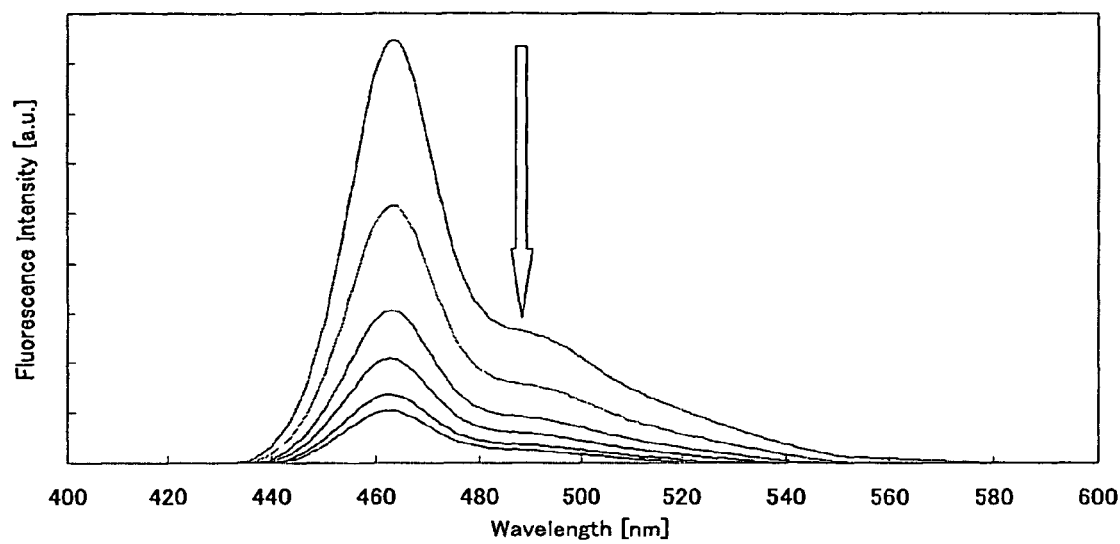
FIG. 3 is a fluorescence spectrum obtained by the formation of complex between a fluorescent molecular wire (S,S)-1 of the present invention and various concentrations of a primary amine.

Next, regarding the fluorescent molecular wire (S,S)-1, the fluorescence quenching behavior due to the formation of complex with a primary amine was examined. The R-form of 2-amino-1-propanol in various concentrations was added to a methylene chloride solution of (S,S)-1 (2.0×10$^{-6}$ M (monomer equivalent)), and the fluorescence spectra were measured (FIG. 3). As shown in FIG. 3, the higher the concentration of amine added is, the higher the degree of fluorescence quenching is.

Figure 4:
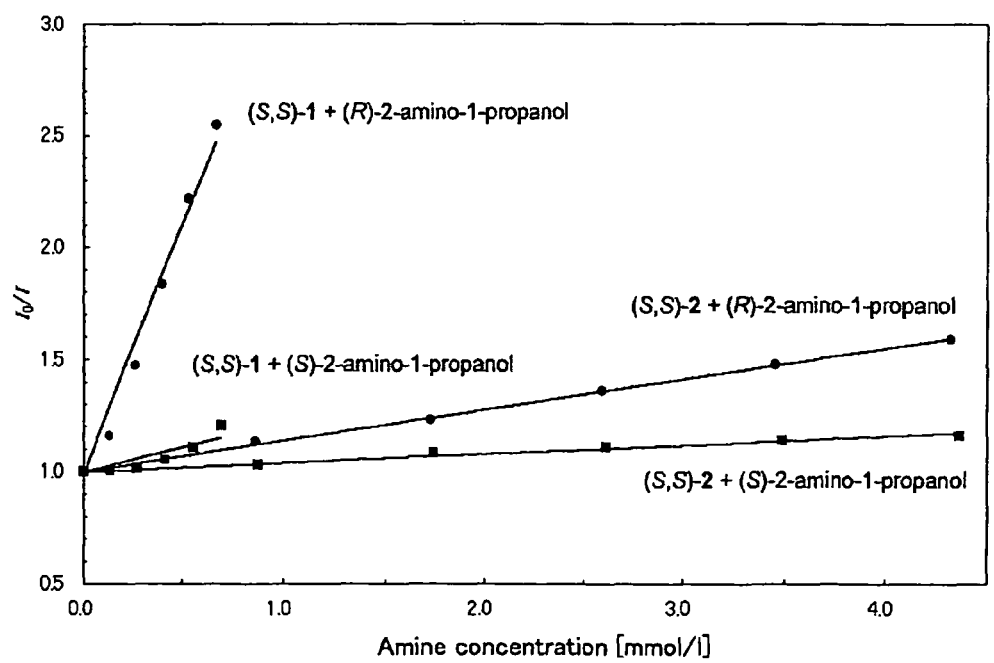
FIG. 4 is a graph showing the relationship between the fluorescence intensity of the fluorescent molecular wire (S,S)-1 of the present invention at 463 nm or a monomer model (S,S)-2 at 432 nm and the concentration of (R)- and (S)-2-amino-1-propanol.

In the case where the R- or S-form of 2-amino-1-propanol was added to the fluorescent molecular wire (S,S)-1 and the monomer model (S,S)-2, changes in the fluorescence intensity at 463 nm at 25° C. were plotted on a graph, thereby examining the detection sensitivity and the asymmetry recognition ability of the both compounds (FIG. 4). The vertical axis of the graph in FIG. 4 shows I$_0$/I, which represents a change in the fluorescence intensity, and the horizontal axis shows the concentration of the amine added (×10$^{-3}$ mol/L). In FIG. 4, solid circles represent (S,S)-1, and solid squares represent (S,S)-2. A greater slope of the graph represents a higher degree of quenching.

As shown in FIG. 4, the degree of quenching of the fluorescent molecular wire (S,S)-1 was significantly higher than that of the monomer model (S,S)-2. In order to obtain respective quenching constants KSV(R) and K$_{SV(S)}$ for complexes formed with the R- and S-forms, the obtained plots were approximated by straight lines according to the Stern-Volmer equation. The quenching constants obtained by calculation were K$_{SV(R)}$=2.2×10$^3$ M$^{-1}$ and K$_{SV(S)}$=2.2×10$^2$ M$^{-1}$, respectively.

The values of the quenching constants of the monomer model (S,S)-2 were respectively K$_{SV(R)}$=1.4×10$^2$ M$^{-1}$ and K$_{SV(S)}$=3.7×10 M$^{-1}$, which were very similar to the complex forming constants (K$_{(R)}$=1.2×10$^2$ M$^{-1}$ and K$_{(S)}$=3.0×10 M$^{-1}$, respectively) obtained from a titration experiment conducted using the ultraviolet and visible absorption spectrum. Therefore, it is found that quenching of the monomer model (S,S)-2 is static quenching resulting from a decrease due to the formation of complex in the concentration of (S,S)-2 that does not form a complex, and signals of the quenching are read out corresponding to the formation of complex in one to one. On the other hand, the values of the quenching constants of the fluorescent molecular wire (S,S)-1 are about 5 to 10 times greater than those of (S,S)-2. This improvement in the sensitivity is due to an effect of amplifying the signal conversion efficiency by the molecular wire method. Moreover, K$_{SV(R)}$/K$_{SV(S)}$, which represents the asymmetry recognition ability, was 10 for (S,S)-1 and 3.6 for (S,S)-2. Thus, from K$_{SV(R)}$/K$_{SV(S)}$, it is also found that (S,S)-1 has superior asymmetry recognition ability to (S,S)-2. The reason for this is uncertain, but it seems that dynamic quenching due to the formation of complex between an excited molecule and an amine or asymmetric induction of the polymer main chain in (S,S)-1 is involved.

The chiral sensor of the present invention has high asymmetry recognition ability toward primary amines and high sensitivity, and thus can be used for optical resolution and analysis of pharmaceuticals, agrochemicals, and the like. In particular, with respect to amines, amino acids, and amino alcohols, it is useful in separation, sensing, sensing for detection of a narcotic drug or identification of the place of production, and the like in connection with their physiological activities. Moreover, it also can be useful in the field of materials such as liquid crystal.

The invention claimed is:

1. A fluorescent molecular wire comprising a polymer main chain having a linked conjugated system, wherein an optically active substituent is linked to the polymer main chain and is conjugated with the polymer main chain, the optically active substituent being represented by the following formula (I):

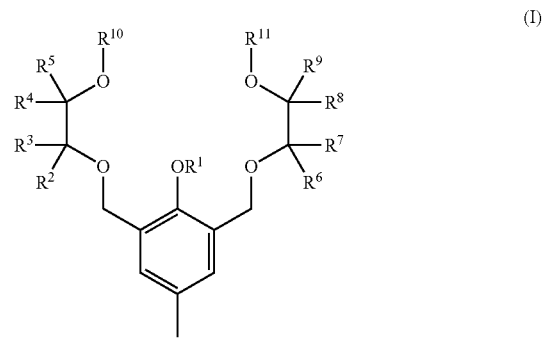

where R$^1$ represents a hydrogen atom or an alkyl group having 1 to 10 carbon atoms R$^2$, R$^3$, R$^4$, R$^5$, R$^6$, R$^7$, R$^8$, and R$^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and R$^3$ and R$^7$ may be bonded respectively to R$^4$ and R$^8$ to form an alkylene group having 2 to 60 carbon atoms that may have a substituent; and R$^{10}$ and R$^{11}$ represent independently a hydrogen atom or an alkyl group having 1 to 15 carbon atoms that may have a heteroatom, and R$^{10}$ and R$^{11}$ may be bonded to form an alkylene group having 2 to 30 carbon atoms that may have a heteroatom, and wherein when a complex between the optically active substituent and a primary amine is formed, a charge transfer from a receptor site to the polymer main chain is caused, thereby resulting in a quenching of the fluorescence in the fluorescent molecular wire, and wherein the polymer main chain having a linked conjugated system is a polyphenylene structure, a polythiophene structure, a poly(phenylene thiophenylene) structure, a poly(phenylene ethynylene) structure, a poly(thiophenylene ethynylene) structure, or a poly(phenylene vinylene)

structure, a polyarylene structure, a poly(arylene ethynylene) structure, or a poly(arylene vinylene) structure.

2. The fluorescent molecular wire of claim 1, wherein the optically active substituent is coupled to the polymer main chain having a linked conjugated system via mono- or poly-arylene, mono- or poly-alkylene, mono- or poly-vinylene, or a combination thereof.

3. The fluorescent molecular wire of claim 1, wherein the optically active substituent is represented by the following formula (II):

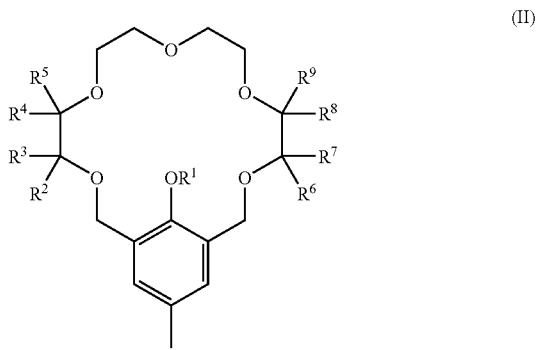

(II)

where $R^1$ represents a hydrogen atom or an alkyl group having 1 to 10 carbon atoms; and $R^2$, $R^3$, $R^4$, $R^5$, $R^6$, $R^7$, $R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent.

4. The fluorescent molecular wire of claim 3, which is represented by the following formula (III):

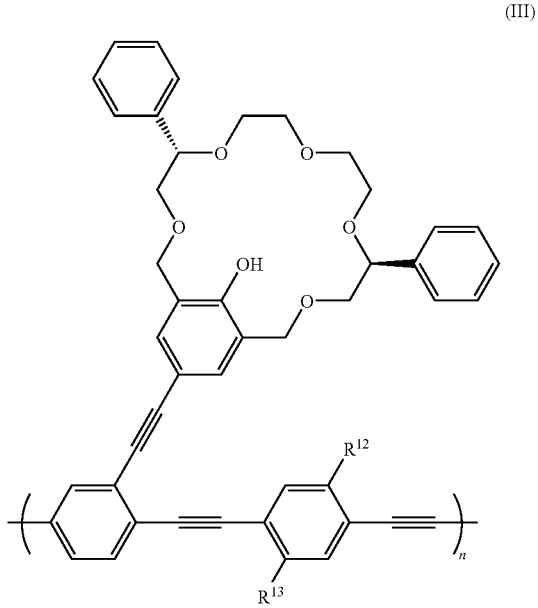

(III)

where $R^{12}$ and $R^{13}$ represent independently a hydrogen atom, an alkyl group having 1 to 20 carbon atoms, an alkoxy group having 1 to 20 carbon atoms, a di- or mono-alkylamide group having 1 to 20 carbon atoms, or an, alkyl ester group having 1 to 20 carbon atoms; and n is an integer of 5 or more.

5. A chiral sensor comprising the fluorescent molecular wire of claim 1.

6. The fluorescent molecular wire of claim 1, wherein the fluorescent molecular wire has an improved asymmetry recognition ability compared to a monomeric compound having the same structure as the optically active substituent.

7. The fluorescent molecular wire of claim 6, wherein the optically active substituent is coupled to the polymer main chain having a linked conjugated system via mono- or poly-arylene, mono- or poly-alkylene, mono- or poly-vinylene, or a combination thereof.

8. The fluorescent molecular wire of claim 2, wherein the optically active substituent is represented by the following formula (II):

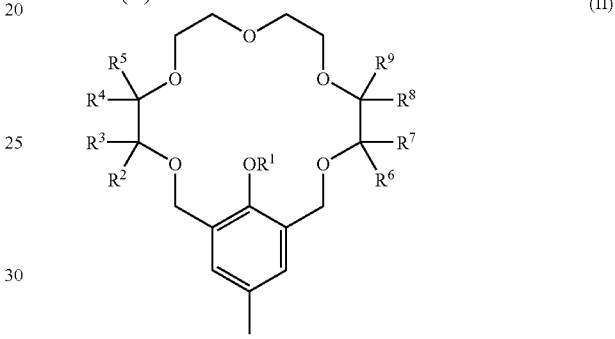

(II)

where $R^1$ represents a hydrogen atom or an alkyl group having 1 to 10 carbon atoms; and $R^2$, $R^3$, $R^4$, $R^5$, $R^6$, $R^7$, $R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an awl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent.

9. The fluorescent molecular wire of claim 6, wherein the optically active substituent is represented by the following formula (II):

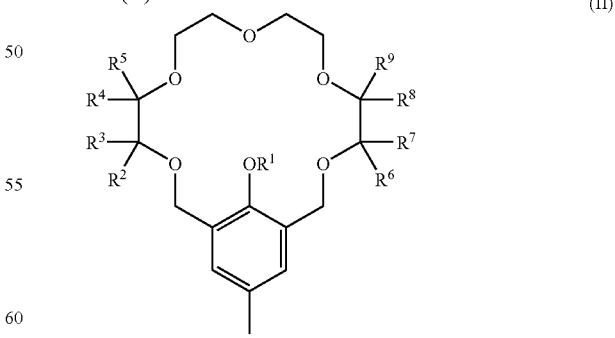

(II)

where $R^1$ represents a hydrogen atom or an alkyl group having 1 to 10 carbon atoms; and $R^2$, $R^3$, $R^4$, $R^5$, $R^6$, $R^7$, $R^8$, and $R^9$ represent independently a hydrogen atom, a linear alkyl group having 1 to 30 carbon atoms that may have a substituent, a branched alkyl group having 2 to 30 carbon atoms that may have a substituent, a cyclic alkyl group having 3 to 30 carbon atoms that may have a substituent, an aryl group having 6 to 30 carbon atoms that may have a substituent, or an aralkyl group having 7 to 30 carbon atoms that may have a substituent, and $R^3$ and $R^7$ may be bonded respectively to $R^4$ and $R^8$ to form an alkylene group having 2 to 60 carbon atoms that may have a substituent.

10. A chiral sensor comprising the fluorescent molecular wire of claim 2.

11. A chiral sensor comprising the fluorescent molecular wire of claim 3.

12. A chiral sensor comprising the fluorescent molecular wire of claim 4.

13. A chiral sensor comprising the fluorescent molecular wire of claim 6.

* * * * *

UNITED STATES PATENT AND TRADEMARK OFFICE
CERTIFICATE OF CORRECTION

| | |
|---|---|
| PATENT NO. | : 7,781,223 B2 |
| APPLICATION NO. | : 10/591920 |
| DATED | : August 24, 2010 |
| INVENTOR(S) | : Tobe et al. |

It is certified that error appears in the above-identified patent and that said Letters Patent is hereby corrected as shown below:

Column 34, line 40, Claim 8, "an awl group" should read -- an aryl group --

Signed and Sealed this

Seventh Day of December, 2010

David J. Kappos
*Director of the United States Patent and Trademark Office*